United States Patent [19]

Kaneko et al.

[11] Patent Number: 5,767,247
[45] Date of Patent: Jun. 16, 1998

[54] ANTI-ANNEXIN-V MONOCLONAL ANTIBODIES, AND PREPARATION AND USE THEREOF

[75] Inventors: Noboru Kaneko, 41-10, Chitosedai 2-chome, Setagaya-ku, Tokyo 157; Ryuko Matsuda, Tokyo; Tadahiro Kajita; Yohsuke Ohta, both of Hyogo-ken, all of Japan

[73] Assignees: Noboru Kaneko; International Reagents Corporation, both of Japan

[21] Appl. No.: 669,509

[22] PCT Filed: Nov. 10, 1995

[86] PCT No.: PCT/JP95/02305

§ 371 Date: Oct. 22, 1996

§ 102(e) Date: Oct. 22, 1996

[87] PCT Pub. No.: WO96/15152

PCT Pub. Date: May 23, 1996

[30] Foreign Application Priority Data

Nov. 11, 1994 [JP] Japan ................................. 6-313958

[51] Int. Cl.⁶ ............................ C07K 16/28; G01N 33/53
[52] U.S. Cl. ...................... 530/388.2; 435/7.1; 435/7.22; 435/7.92; 435/7.94; 435/332; 435/346
[58] Field of Search ..................... 435/7.1, 7.92, 435/7.94, 332, 346, 7.22; 530/388.2

[56] References Cited

PUBLICATIONS

Takei, N. et al. "Neurotrophic effects of annexin V on cultured neurons from embryonic rat brain", Neuroscience Letters (Apr., 1994) vol. 171, Nos. 1 to 2, pp. 59–62.

Sun, J. et al. "Nucleolar and cytoplasmic localization of annexin V", FEBS Lett. (1992), vol. 314, No. 3, pp. 425–429.

Culard, J. et al. "Characterization and subcellular localization of calcium–dependent phospholipid binding proteins (annexins) in normal human skin and reconstituted epidermis", J. Invest. Dermatol. (1992) vol. 98, No. 4, pp. 436–441.

Kaneko, N. et al. "Purification of cardiac annexin V from beagle dog heart and changes in its localization in the ischemic rat heart", (May 1994) vol. 9, No. 3, pp. 148–154.

Romisch, J et al. Blood Coagulation and Fibrinolysis. 3:11–17, Mar. 1992.

Seaver, Sally S. Genetic Engineerin News. 14(14): 10,21, Aug. 1994.

Harlow, E. and Lane, DP. Antibodies: A Laboratory Manual. Cold Spring Harbor Laboratory, Cold Spring Harbor, NY. pp. 72–77, 92–97, 128–135, 141–157, 460 and 578–581, 1988.

Romisch J and Heimburger, N. Biol. Chem. Hoppe–Seyler. 371: 383–388, May 1990.

*Primary Examiner*—David Saunders
*Assistant Examiner*—F. Pierre VanderVegt
*Attorney, Agent, or Firm*—Ostrolenk, Faber, Gerb & Soffen, LLP

[57] ABSTRACT

Using human annexin-V or human annexin-V plus dog annexin-V as antigen(s), hybridoma cell lines are prepared which are capable of producing anti-annexin-V monoclonal antibodies having a binding specificity to antigenic determinant site on annexin-V as antigenic protein and belonging to immunoglobulin G class. By the hybridoma cell lines are produced the anti-annexin-V monoclonal antibodies, with which a diagnostic agent is provided for diagnosis of myocardial infarction and angina pectoris. There is also provided diagnosis of myocardial infarction and angina pectoris using a first and a second monoclonal antibodies produced by the hybridoma cell lines to quantitate human annexin-V in a sample, in which an antigen-antibody reaction on annexin-V in the sample is caused with the first anti-annexin-V monoclonal antibody to form an annexin-V antigen/anti-annexin-V monoclonal antibody complex, the antigenic site of annexin-V of the formed annexin-V antigen/annexin-V monoclonal antibody complex is allowed to be bound with a labeled anti-annexin-V polyclonal or second monoclonal antibody so as to form a labeled form of said annexin-V antigen/anti-annexin-V monoclonal antibody complex bound with the polyclonal or the second monoclonal antibody, and the labeled form of the complex is quantitatively analyzed.

19 Claims, 13 Drawing Sheets

F I G. 1
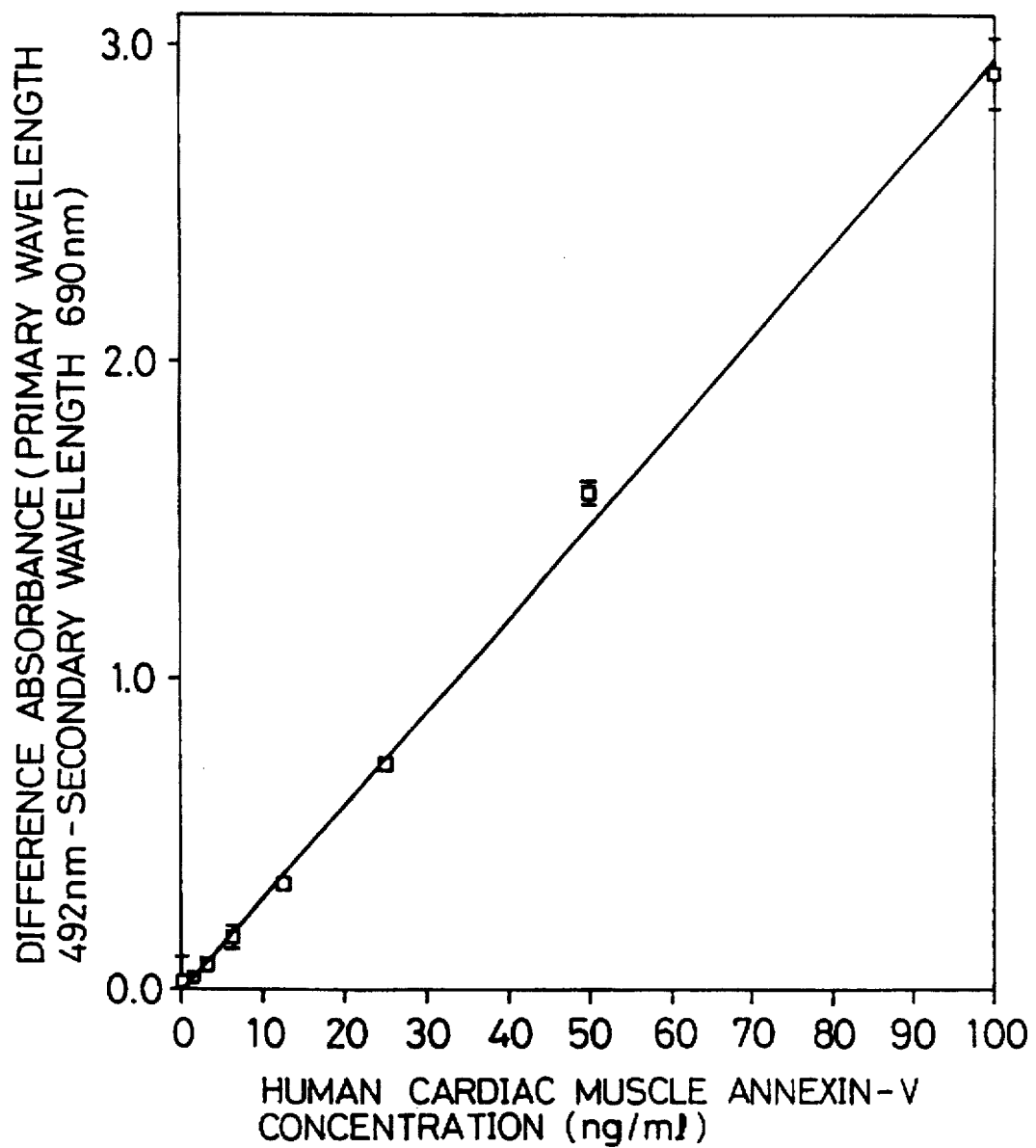

F I G. 9
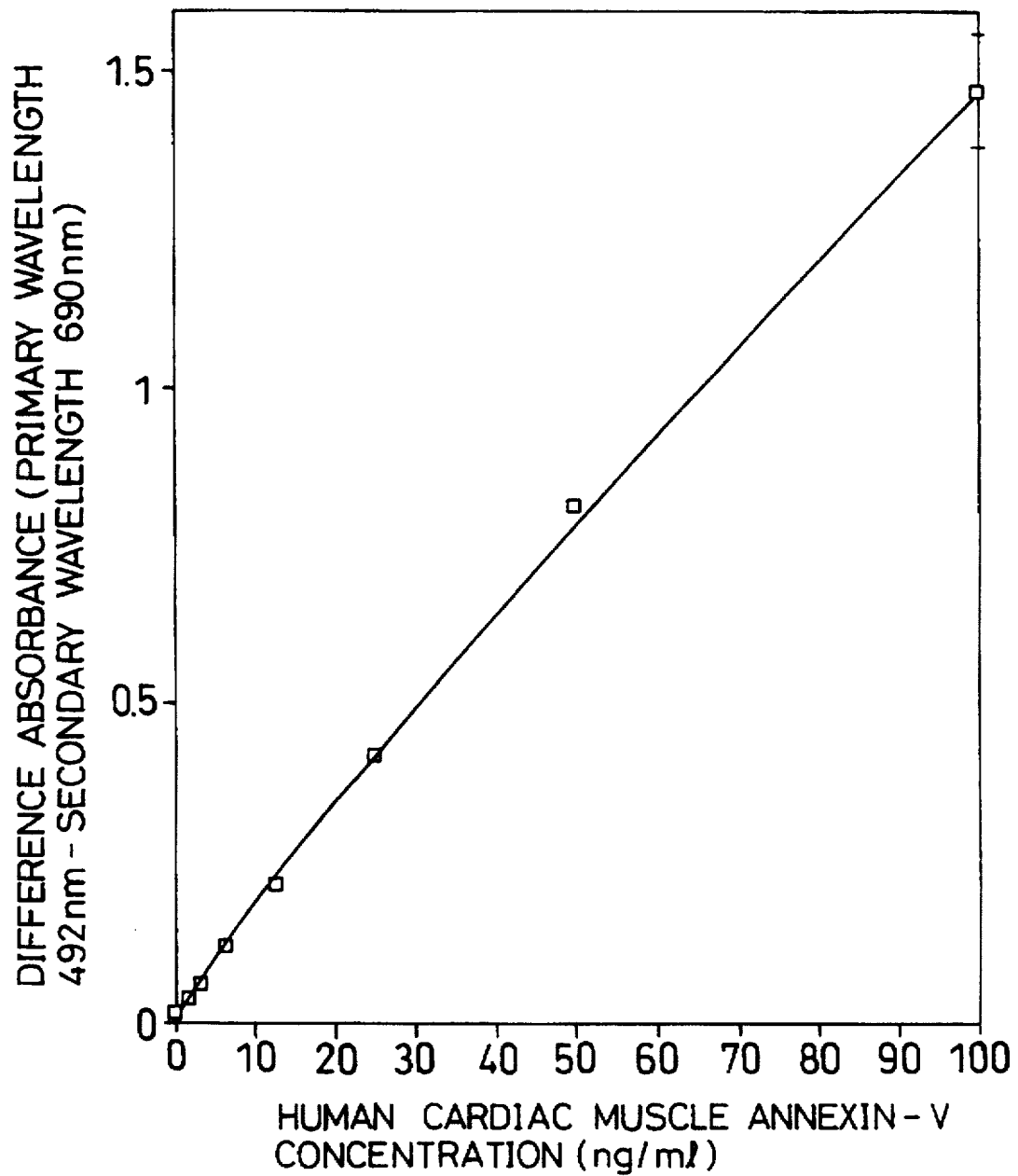

1

ANTI-ANNEXIN-V MONOCLONAL ANTIBODIES, AND PREPARATION AND USE THEREOF

TECHNICAL FIELD

The present invention relates to anti-annexin-V monoclonal antibodies having binding specificities to antigenic determinant sites on annexin-V, a protein present in blood, plasma and/or serum of humans and mammalian animals, and, more particularly, to such anti-annexin-V monoclonal antibodies suitable for use in the immunological determination of the concentration of human annexin-V in the blood, plasma and/or serum, being present particulary in the human cardiac muscles as a marker of myocardial infarction and angina pectoris.

The present invention further relates to hybridoma cell lines producing said anti-annexin-V monoclonal antibodies and, more particularly, to such hybridoma cell lines producing the monoclonal antibodies for use in the detection and quantitative analysis of human cardiac-muscle annexin-V as a marker of myocardial infarction and angina pectoris.

The present invention also relates to a method for the detection of annexin-V in a sample and, more particularly, to a method for the detection or quantitative analysis of human cardiac-muscle annexin-V in the blood and/or serum as a marker of myocardial infarction and angina pectoris. The present invention further relates to human cardiac muscle annexin-V in the plasma and/or serum, monoclonal antibodies for use in the detection and quantitative analysis thereof and hybridoma producing such monoclonal antibodies.

In addition, the present invention relates to the development and utilization of anti-annexin-V antibodies for the measurement of annexin-V of humans and mammals and the hybridoma cell lines producing such antibodies and, more particularly, to the development and utilization of the anti-human-annexin-V antibodies for use in quick diagnosis of diseases causing sudden cellular necrosis such as myocardial infarction and angina pectoris causing an ischemic disorder, through the concentration measurement of annexin-V, a protein in the cells or blood.

BACKGROUND ART

Annexin is a calcium-binding protein being present in tissues and cells of humans and various animals, particularly in their cytoplasmic solubles. This protein is composed of families defined by the amino acid sequences and, at present, annexin I through XII are known. The protein binds to phospholipids and actin depending upon the calcium concentration, and is known to have anti-inflammatory and anticoagulant functions.

In patients suffering from tissue or cellular necrosis, due to myocardial infarction, for example, various substances contained in the necrosed cardiac-muscle cells leak into blood. The current diagnosis of acute myocardial infarction is conducted by detecting such substances in the blood and the substances are generally called myocardial-infarction markers.

Such myocardial-infarction markers to be measured in biochemical tests for use in the diagnosis of acute myocardial infarction include LD-1, AST, creatin kinase (CK), creatin kinase MB-fraction (CK-MB), myoglobin, lactic dehydrogenase (LDH), myosin light-chain L and troponin-T (TnT). While the results or the analytical values of these myocardial-infarction markers may be employed independently or in combination in the diagnosis of myocardial-infarction, the prevailing method is to employ them in combination.

In the case of an ischemic disease such as angina pectoris, arrhythmia is observed arrhythmia within several hours after the onset of the attack, and may lead to arrhythmia death. Quick diagnosis and treatment at the early stage are therefore needed in myocardial infarction and angina pectoris.

However, regarding the above-mentioned various types of myocardial-infarction markers (all are substances leaking from the cardiac muscles into the blood) to be examined in biochemical tests for the diagnosis of acute myocardial-infarction, it has been reported that such myocardial-infarction markers reach their respective peak concentrations in the blood 7 to 78 hours after the attack of myocardial infarction. In addition, the time in which the myocardial infarction markers reach the maximal or peak concentration in the blood may vary considerably from one patient to another. Thus, these markers for the diagnosis of myocardial infarction are considered to be problematic since they make it difficult to establish a quick diagnosis of myocardial infarction and hence they do not contribute to quick selection of therapeutic measures for the patients.

The employment of the results obtained by measuring two or more markers of the aforesaid myocardial-infarction markers for more reliable diagnosis of myocardial infarction is also problematic and far from meeting the need for early-stage therapy of myocardial infarction patients because it takes a long time for the respective myocardial-infarction markers to reach the maximal (peak) concentrations in the blood and such time varies depending upon the patient examined.

In the case of angina pectoris, marker substances to be examined in biochemical tests for diagnozing the disease have not yet been identified. Thus, biochemical diagnosis of angina pectoris is generally considered to be difficult and a need is felt for the establishment of diagnosis for angina pectoris through biochemical tests.

The present invention is directed to overcoming the problems in the conventional biochemical tests so as to enable quick diagnosis of myocardial infarction and angina pectoris.

DISCLOSURE OF THE INVENTION

It has been found that, among annexin-proteins present in human cardiac muscles, human annexin-V, occurring in the solubles of the cardiac-muscle cells and having a molecular weight of 35,000, i.e. smaller than that of creatin kinase (81,000), generally leaks from the necrosed cardiac muscles of myocardial-infarction or angina-pectoris patients in the early stage of the diseases. Thus the present applicant has already disclosed a method for determining the concentration of human annexin-V in human blood, plasma and/or serum and a method for diagnosing myocardial infarction and/or angina pectoris, using dog cardiac-muscle annexin-V polyclonal antibodies which specifically cross-react with such human annexin-V (Japanese Laid-Open Pat. Application No.72147/1995).

Thus, human annexin-V is a novel marker of myocardial infarction whose concentration (in the blood, plasma and serum) reaches the peak within one to several hours after the attack of myocardial infarction.

The present inventors therefore made extensive studies to provide antibodies capable of specifically recognizing human annexin-V and suitable for use in a method for the assay of human annexin-V in a sensitive, simple and quick manner and found that hybridoma cells, obtained from anti-human-annexin-V-producing lymphocytes and myeloma cells using the conventional cell fusion technique, produce stable anti-human-annexin-V monoclonal antibodies meeting the above-mentioned object for the completion of the present invention.

The present invention relates to an improvement on the invention of the aforesaid application and is directed to the provision of diagnostic agents and diagnostic methods, by which highly reliable diagnosis of myocardial infarction and/or angina pectoris can be made in a short time after the attack of myocardial infarction or angina pectoris, as well as the provisions of detection substances for detecting and quantitatively analyzing the myocardial-infarction marker or angina pectoris marker and the preparation and use thereof.

Thus, the present invention is directed to an anti-annexin-V monoclonal antibody characterized by having a binding specificity to antigenic determinant site on annexin-V as antigenic protein and belonging to immunoglobulin G class, to a hybridoma cell line characterized by being capable of producing an anti-annexin-V monoclonal antibody having a binding specificity to antigenic determinant site on annexin-V as antigenic protein and belonging to immunoglobulin G class, to a diagnostic agent for myocardial infarction and angina pectoris characterized by comprising an anti-annexin-V monoclonal antibody having a binding specificity to antigenic determinant site on annexin-V as antigenic protein and belonging to immunoglobulin G class, and also to a diagnostic agent for myocardial infarction and angina pectoris characterized by comprising a reagent containing a first anti-annexin-V monoclonal antibody having a binding specificity to antigenic determinant site on annexin-V as antigenic protein and belonging to immunoglobulin G class and a reagent containing a second anti-annexin-V monoclonal or polyclonal antibody having a binding specificity to antigenic determinant site on annexin-V as antigenic protein and belonging to immunoglobulin G class, with the second antibody being labeled.

In addition, the present invention is directed to a method for diagnosing myocardial infarction and angina pectoris characterized by comprising an antigen-antibody reaction of annexin-V in a sample with an anti-annexin-V monoclonal antibody to form an annexin-V antigen/anti-annexin-V monoclonal antibody complex and assaying the formed annexin-V antigen/anti-annexin-V monoclonal antibody complex, to a method for diagnosing myocardial infarction and angina pectoris characterized by comprising causing an antigen-antibody reaction of annexin-V in a sample with an anti-annexin-V monoclonal antibody to form an annexin-V antigen/anti-annexin-V monoclonal antibody complex, allowing the antigenic site of annexin-V of the formed annexin-V antigen/anti-annexin-V monoclonal antibody complex to bound with a labeled anti-annexin-V polyclonal or monoclonal antibody so as to form a labeled form of said annexin-V antigen/anti-annexin-V monoclonal antibody complex bound with the polyclonal or monoclonal antibody, and quantitatively analyzing the labeled form of the complex, to a method for analyzing human cardiac muscle or related annexin-V in a sample characterized by comprising causing an antigen-antibody reaction of human annexin-V in the sample with an anti-annexin-V monoclonal antibody to form an annexin-V antigen/anti-annexin-V monoclonal antibody complex and quantitatively analyzing the formed annexin-V antigen/anti-annexin-V monoclonal antibody complex, and also to a method for analyzing annexin-V in a sample characterized by comprising causing an antigen-antibody reaction of human annexin-V in the sample with a first anti-annexin-V monoclonal antibody having a specificity to antigenic determinant site on annexin-V antigenic protein to form an annexin-V antigen/anti-annexin-V monoclonal antibody complex, allowing the antigenic site of human annexin-V of the formed annexin-V antigen/anti-annexin-V monoclonal antibody complex to be bound with an anti-annexin-V polyclonal or second monoclonal labeled antibody so as to form a labeled form of said annexin-V antigen/anti-annexin-V monoclonal antibody complex bound with the polyclonal or the second monoclonal antibody, and quantitatively analyzing the labeled form of the complex.

The present invention is further directed to a method for preparing anti-annexin-V monoclonal antibodies which comprises fusing lymphocytes induced from mice immunized with annexin-V with myeloma cells to form hybridoma cells, and growing the formed hybridoma cells to produce anti-annexin-V monoclonal antibodies having binding specificities to antigenic determinant sites on annexin-V antigenic protein.

Human annexin-V to be used as the antigen in the present invention is a protein which may have a molecular weight of 32 to 35 kilodalton and may be one occurring in the human heart.

The human heart to be used in the present invention is one extracted from a human cadaver and maintaining its activities.

The antigen protein—human annexin-V protein occurring in human heart—is found in the soluble fractions of the heart and purified by removing the connective tissues and lipids from the cardiac tissue of a human cadaver. The hybridoma cell lines to be used in the present invention for producing anti-human annexin-V monoclonal antibodies are formed by means of the cell fusion of lymphocytic cells with myeloma cells, in which the lymphocytic cells are spleen (a lymphoid organ) including spleen cells and white pulp of spleen or plasmablast cells prepared from lymph nodes (e.g. lymphoid nodule) and being in the process of the differentiation to plasma cells, from a mammalian animal such as a mouse or the like which was immunized with human annexin-V as the antigen extracted and purified from human cardiac tissue.

The myeloma cell strain to be used in the present invention is generally a hypoxanthine-guanine-phosphoribosyltransferase (HGPRT)-deficient one or thymidine-kinase(TK)-deficient one. The HGPRT-deficient strains suitable for use include 8-azaguanine(8-AG)-resistant strain and 6-thioguanine(6-TG)resistant strain while the TK-deficient strains suitable for use include bromodeoxyuridine(BUdR)-resistant strain.

The cell fusion is conducted using a cell fusion accelerator, in which polyethylene glycol (PEG) is primarily used for the cell fusion in the present invention.

The cell fusion accelerators usable in the present invention include, by substance name or trade name, PEG600, PEG400, PEG1000, PEG3000, PEG6000, GLUCAM™ E-10, GLUCAM™ E-20, GLUCAM™ P-10, polyethylene glycol methyl ester (PEG methyl ester) (molecular weight: 350, 2000 and 5000), PEG 1000, polyglycol P15-200, pluronic F38 polyol Prilled, Decaglycerol, Camul 101 Butyrate, Tetronic 304 polyol, triglycerol, polyvinylpyrrolidone (molecular weight: 1000) and glycerin.

The anti-human-annexin-V monoclonal antibodies in the present invention can be produced by fusing lymphocytic plasmablast cells extracted from the lymphoid organs of mice or other animals immunized against annexin-V as the antigen with myeloma cells to form hybridomas and growing the hybridomas with, for example, a HAT culture medium, in which the hybridomas for the selective proliferation are, for example, anti-human-annexin-V-monoclonal-antibody-producing hybridoma cell lines HCA-627 and HDA-907 deposited on Aug. 16, 1994 and Nov. 7, 1995, respectively, at the National Institute of Bioscience and Human-Technology, the Agency of Industrial Science and Technology of Japan, an International Depositary Authority for the deposit of microorganism, under the numbers FERM BP-5284 and FERM BP5286, respectively.

The selection of the hybridoma cell lines can be made through a HAT-selection, an ouabain-selection or the like.

The anti-human-annexin-V monoclonal antibodies in the present invention can be obtained by culturing the above-mentioned hybridoma clones by a conventional culture process such as the high density culture process, the spinner-flask culture process or the like and purifying the antibodies from the culture supernatant by means of affinity chromatography using a carrier bound with protein-A or a carrier bound with anti-mouse-immunoglobulin.

In the present invention, the anti-human-annexin-V monoclonal antibodies can be produced by injecting the hybridoma cell lines obtained through the above-mentioned culture into the abdominal cavities of prestene-pretreated immunocompromised mice, salting out, with ammonium sulfate or sodium sulfate, the ascitic fluid induced by the hybridoma cell lines, and purifying the fluid by means of ion-exchange chromatography using DEAE cellulose to obtain the immunoglobulin (IgG) fractions.

A hybridoma cell line as termed with respect to the present invention means not only a hybridoma cell just obtained by cell-fusion but also hybridoma cells at any passages subsequent to the primary culture.

The screening for the resultant hybridoma cell lines can be conducted by detecting the anti-human-annexin-V monoclonal antibodies secreted by the hybridomas in the culture by such methods as immunoassay, radioimmunoassay and ELISA.

In the present invention, the process of screening for the hybridoma cell lines has been found to be able to obtain various anti-human-annexin-V monoclonal antibodies having different specific reactivities with human-annexin-V antigen.

By a method similar to that for producing anti-human-annexin-V monoclonal antibodies there can be obtained anti-annexin-V monoclonal antibodies having specific reactivities with the antigenic determinant sites of the annexin-V antigens of dogs and other mammalian animals, by immunizing the mammalian animals with the annexin-V antigens derived from dogs or the like, cell-fusing the lymphocytic cells with myeloma cells to produce the hybridoma cell lines.

The anti-annexin-V monoclonal antibodies in the present invention are defined to include such anti-annexin-V monoclonal antibodies from mammalian animals as well as anti-human-annexin-V monoclonal antibodies.

Thus, cloning is carried out for the hybridoma cell lines which have been screened for the ability to secrete anti-human-annexin-V monoclonal antibodies.

The cloning of the hybridoma cell lines in the present invention can be made by such techniques as limiting dilution, soft agar method, fibrin gel method, cell sorter method and the like.

The hybridoma cell lines with an ability to produce anti-human-annexin-V monoclonal antibodies thus obtained are subjected to a large-scale fermentation to produce anti-human-annexin-V monoclonal antibodies.

The anti-human-annexin-V monoclonal antibodies of the present invention have specific reactivities with the antigenic determinant sites of human annexin-V, a protein antigen. They are antibodies featuring an antigen-antibody reaction with the antigenic protein (human annexin-V) and will thus bind to human annexin-V present in human blood, plasma and/or serum, thereby enabling highly specific and sensitive detection and quantitative analysis of human annexin-V in human blood, plasma and/or serum through such techniques as immunoassay, radioimmunoassay, ELISA and the like.

The anti-human-annexin-V monoclonal antibodies of the present invention exhibit specific reactivities with the antigenic determinant sites of human annexin-V, a protein occurring in the human heart, thereby enabling highly specific and sensitive detection and/or quantification of human annexin-V in the blood, plasma and/or serum, through such techniques as immunoassay, radioimmunoassay, ELISA and the like, as they bind to the antigenic protein, human annexin-V, present in the human blood, plasma and/or serum.

While human annexin-V concentration in the blood of a normal adult is found, for example, to be 5.6 ng/ml at the highest, it has been found by the application of the present invention that the human annexin-V concentration with a patient suffering myocardial infarction may be, for example, as high as 90 ng/ml even in the stage when the CK value indicated is normal and also that the human annexin-V concentration of a patient suffering angina pectoris may be as high as 29 ng/ml even in the stage when the CK value indicated is normal. The present invention therefore enables a diagnosis of the diseases at earlier stages than possible with the conventional diagnosis based on the CK value.

BRIEF DESCRIPTION OF THE DRAWINGS

FIG. 1 illustrates a calibration curve for use in ELISA system for a working example, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-155H, an anti-human-annexin-V monoclonal antibody-producing hybridoma cell line clone, and having a specific activity with human annexin-V, and another anti-human-annexin-V monoclonal antibody as the solid phase, produced by HCA-290, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 2:
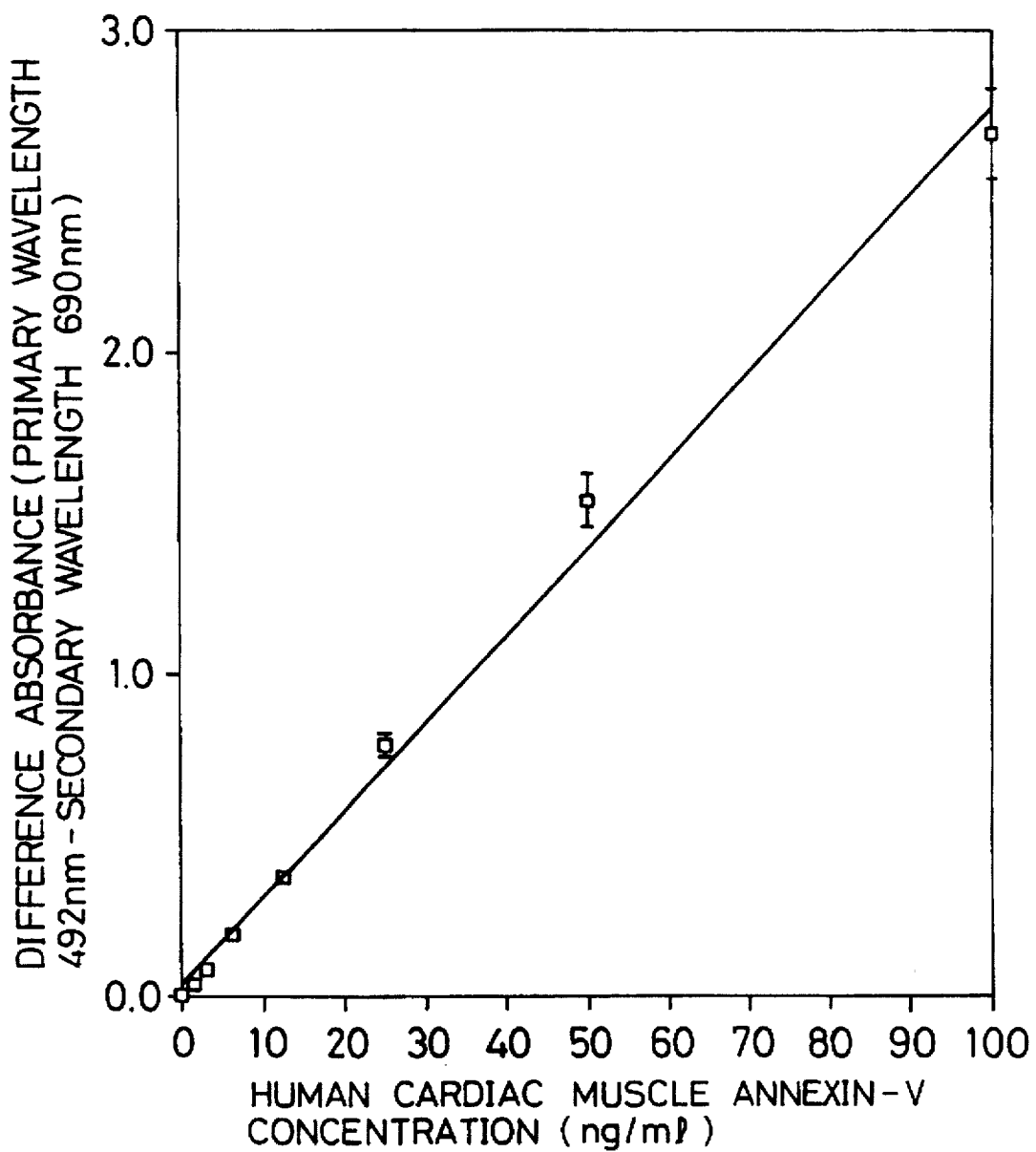

FIG. 2 illustrates a calibration curve for use in ELISA system for another working example, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-155H, an anti-human-annexin-V monoclonal antibody-producing hybridoma cell line clone, and having a specific activity with human annexin-V, and another anti-human-annexin-V monoclonal antibody as the solid phase, produced by HCA-57HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 3:
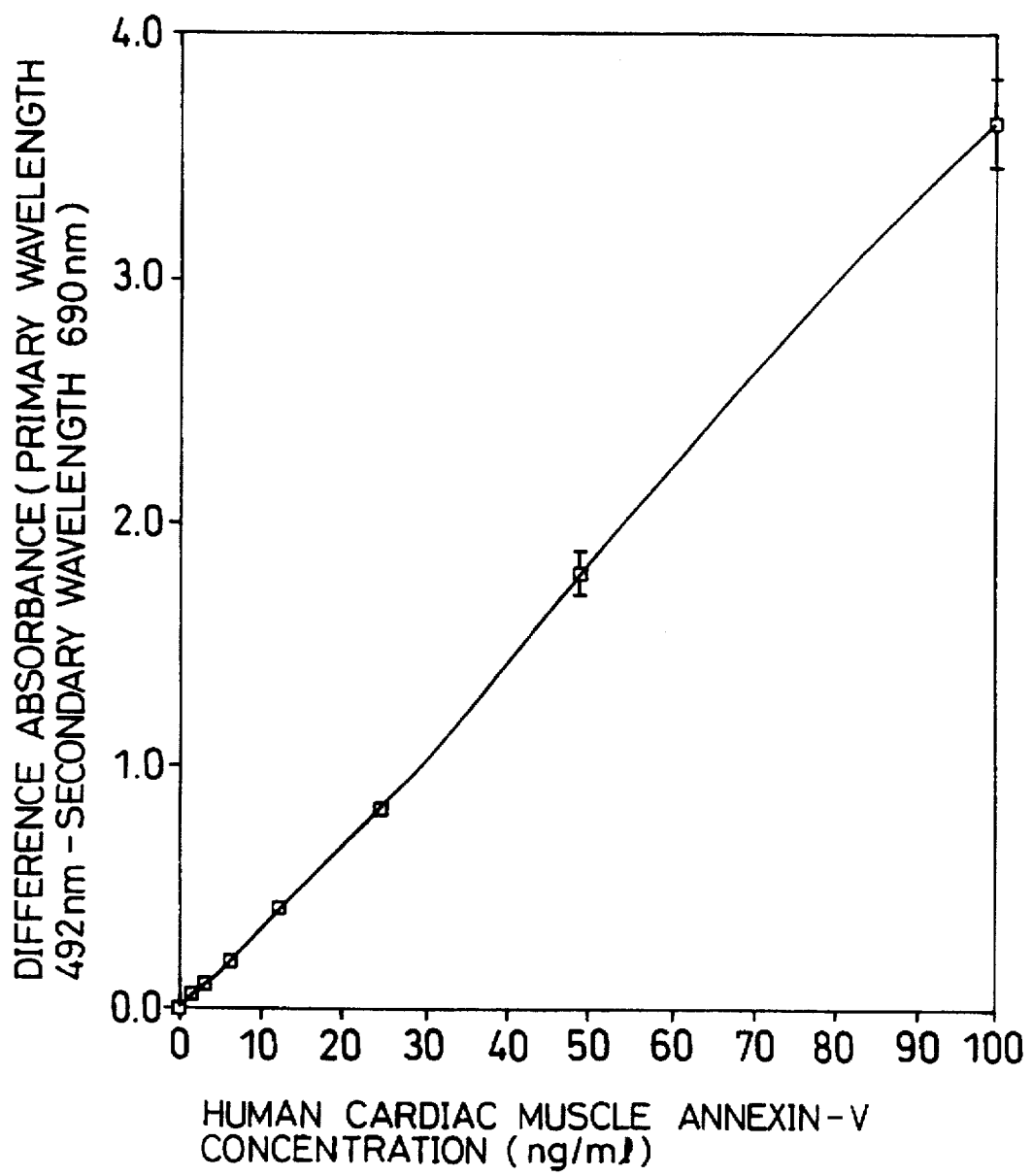

FIG. 3 illustrates a calibration curve for use in ELISA system for a further working example different from the examples as shown by FIGS. 1 and 2, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-155H, an anti-human-annexin-V monoclonal antibody-producing hybridoma cell line clone, and having a specific activity with human annexin-V, and another anti-human-annexin-V monoclonal antibody as the solid phase, produced by HCA-293HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length the arrows extending upward or downward from each □ mark represents the average ±2 SD respectively.

Figure 4:
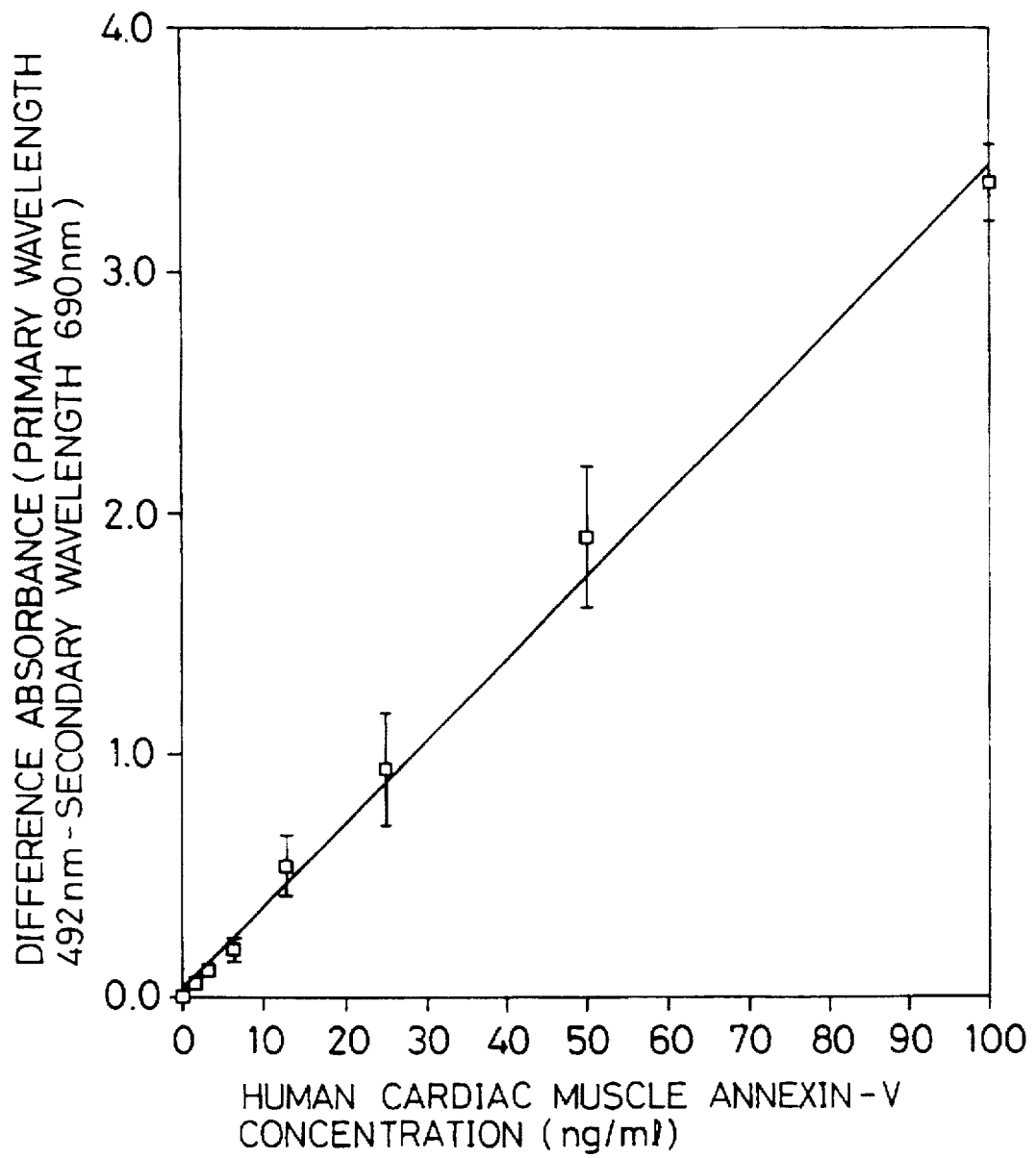

FIG. 4 illustrates a calibration curve for use in ELISA system for a still further working example different from the examples as shown by FIGS. 1 through 3, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-155H, an anti-human-annexin-V monoclonal antibody-producing hybridoma cell line clone, and having a specific activity with human annexin-V, and another anti-human-annexin-V monoclonal antibody as the solid phase, produced by HCA-350HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 5:
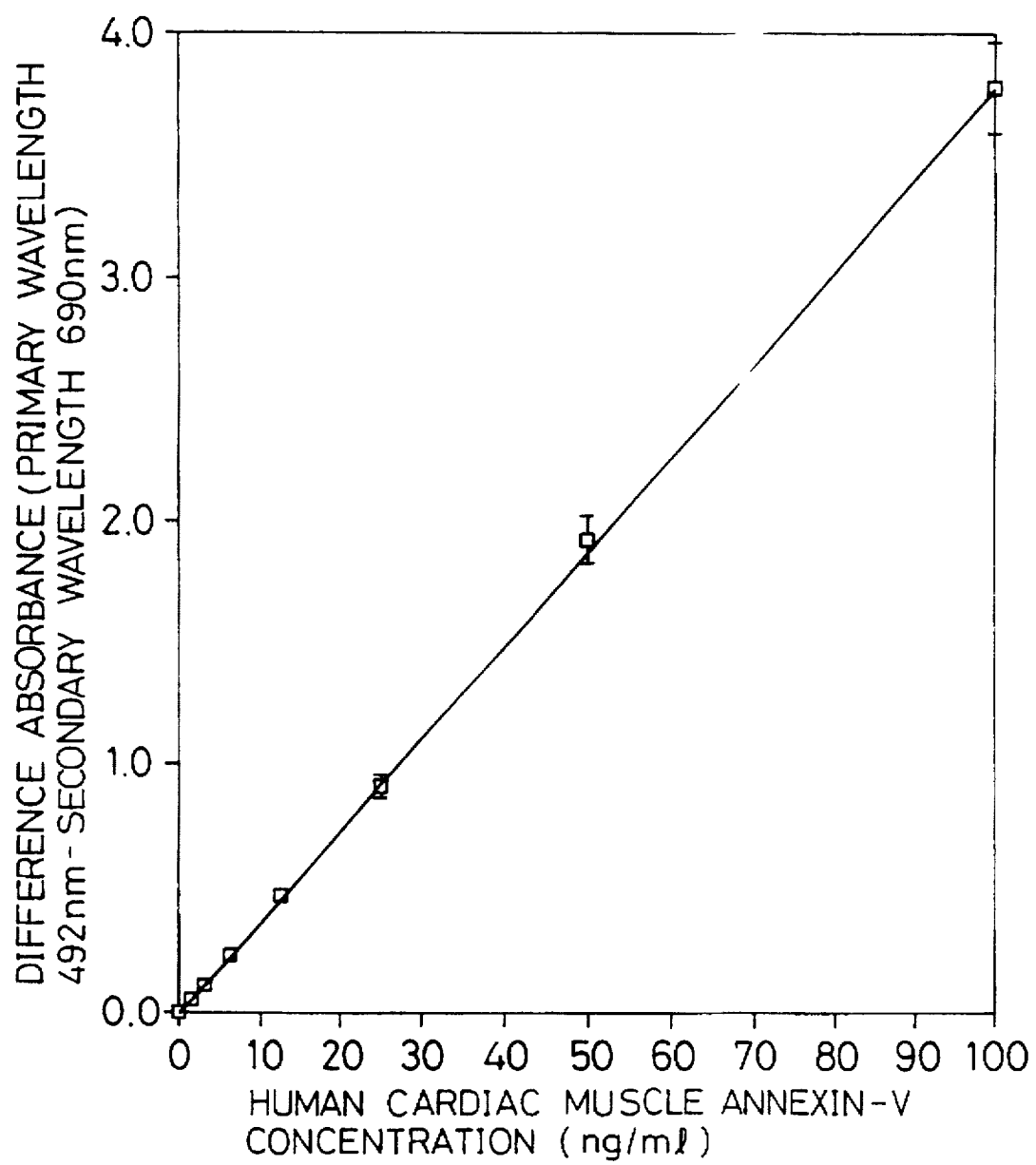

FIG. 5 illustrates a calibration curve for use in ELISA system for a working example different from the examples as shown by FIGS. 1 through 4, in which the anti-human-annexin-V monoclonal antibodies of the present invention are employed to determine the concentration of. 8M-urea-treated human annexin-V. The ELISA system is made up of a combination of a HRPO-labeled anti-human-annexin-V monoclonal antibody produced by HCA-660HD, an anti-human-annexin-V monoclonal antibody-producing hybridoma cell line clone, and having a specific activity with human annexin-V, and another anti-human-annexin-V monoclonal antibody as the solid phase, produced by HCA-290HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 6:
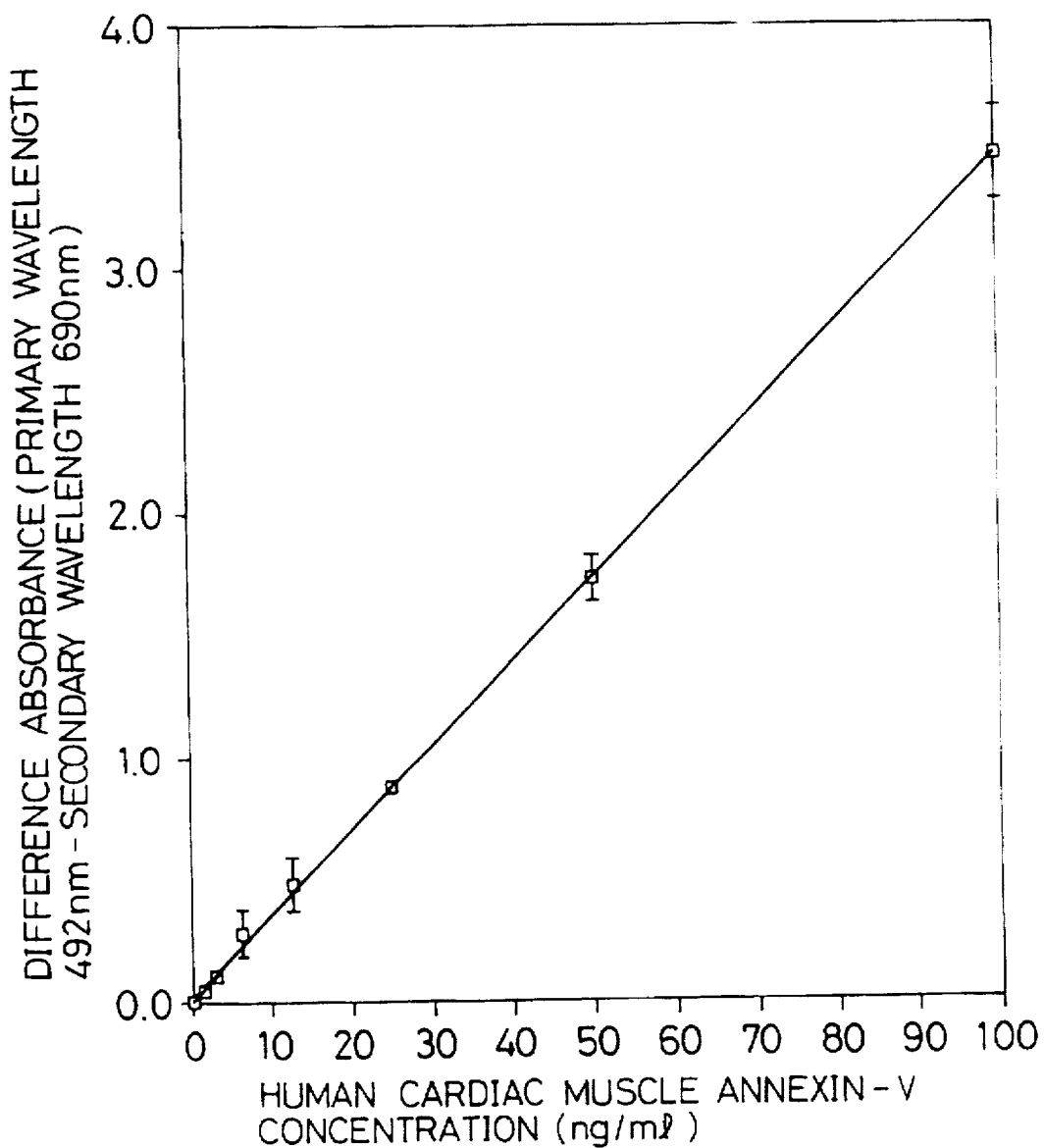

FIG. 6 illustrates a calibration curve for use in ELISA system for a further working example different from the examples as shown by FIGS. 1 through 5, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-660HD, an anti-human-annexin-V monoclonal antibody-producing hybridoma cell line clone, and having a specific activity with human annexin-V, and another anti-human-annexin-V monoclonal antibody as the solid phase, produced by HCA-57HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 7:
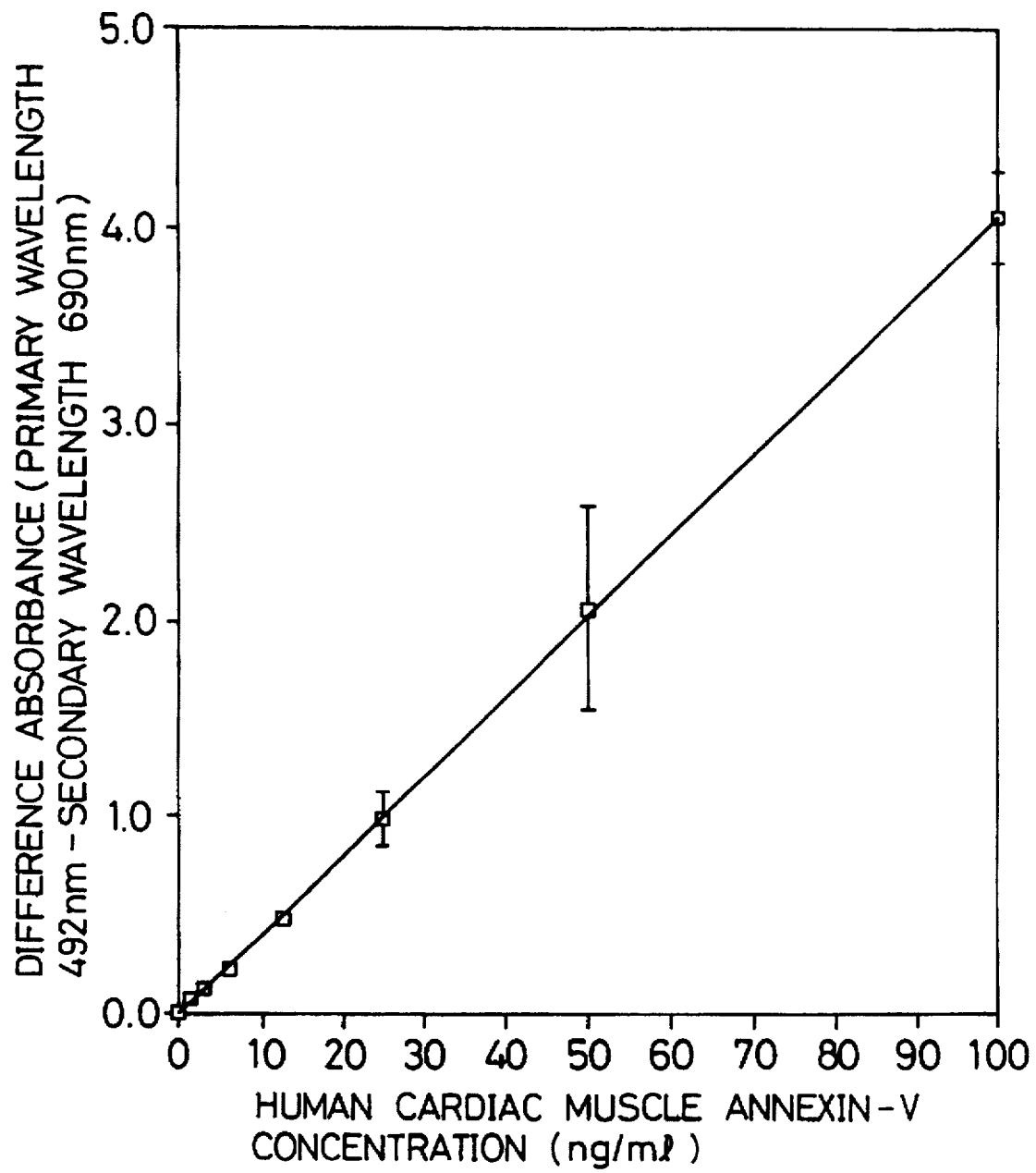

FIG. 7 illustrates a calibration curve for use in ELISA system for a still further working example different from the examples as shown by FIGS. 1 through 6, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-660HD, an anti-human-annexin-V monoclonal antibody-producing hybridoma cell line clone, and having a specific activity with human annexin-V, and another anti-human-annexin-V monoclonal antibody as the solid phase, produced by HCA-293HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 8:
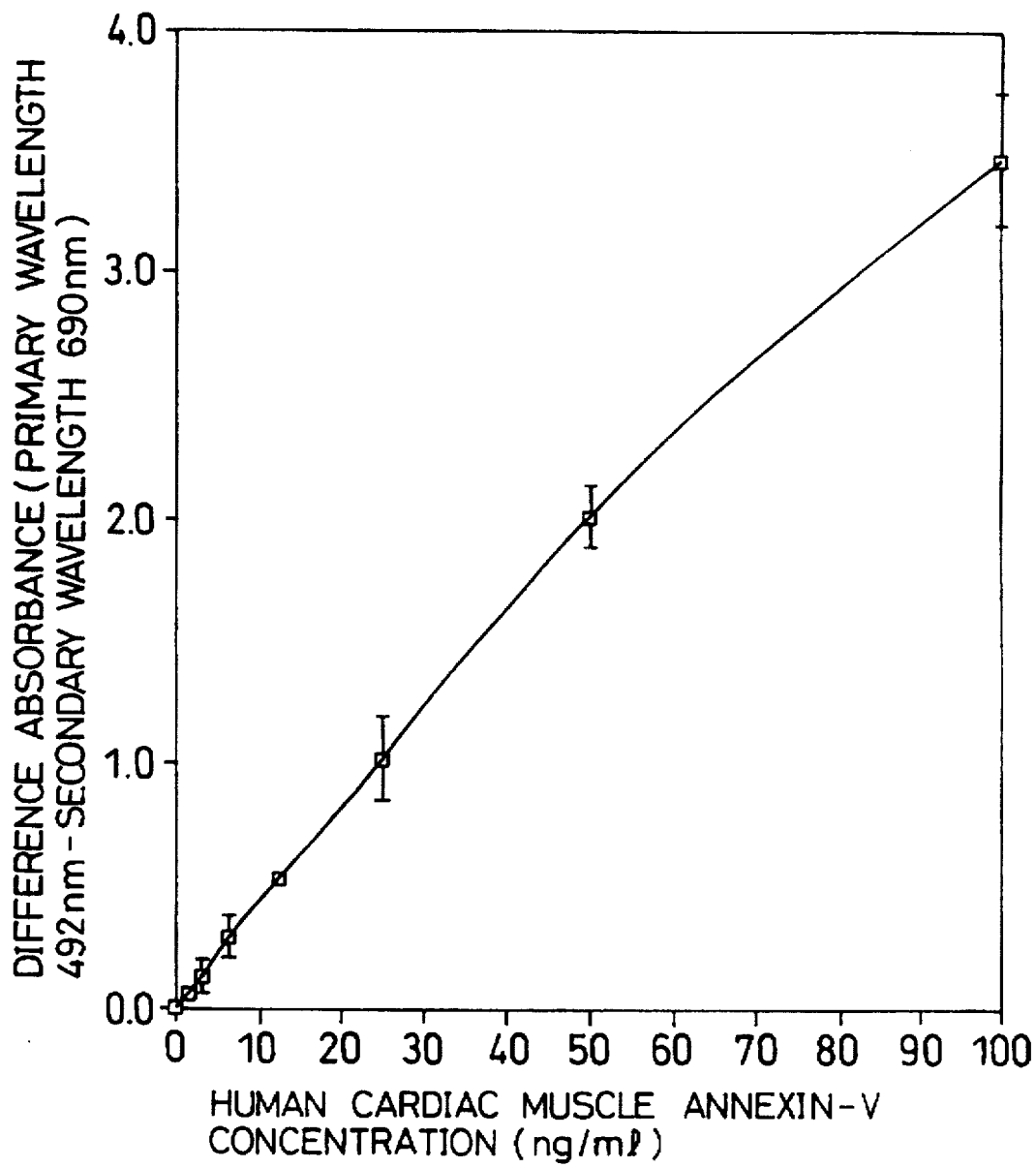

FIG. 8 illustrates a calibration curve for use in ELISA system for another working example different from the examples as shown by FIGS. 1 through 7, in which the anti-human-annexin-V monoclonal antibodies of the present invention are employed to determine the concentration of 8M-urea-treated human annexin-V. The ELISA system is made up of a combination of a HRPO-labeled anti-human-annexin-V monoclonal antibody produced by HCA-660HD, an anti-human-annexin-V monoclonal antibody-producing hybridoma cell line clone, and having a specific activity with human annexin-V, and another anti-human-annexin-V monoclonal antibody as the solid phase, produced by HCA-350HDR, another anti-human-annexin-V monoclonal antibody-producing hybridoma cell line clone, and having a specific activity with human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each mark represents the average difference absorbance with the arrows extending upward or downward from each □ mark represents the average ±2SD respectively.

FIG. 9 illustrates a calibration curve for use in ELISA system for a working example, in which the anti-human-annexin-V monoclonal antibodies of the present invention are employed to determine the concentration of native human annexin-V. The ELISA system is made up of a combination of a HRPO-labeled anti-dog-32KP polyclonal antibody, and an anti-human-annexin-V monoclonal antibody as the solid phase, produced by HCA-627, an anti-human-annexin-V monoclonal antibody-producing hybridoma cell line clone, deposited under the number FERM BP-5284 at the International Depositary Authority for the deposit of microorganisms and having a specific activity with native human annexin-V.

In the Figure, the ordinate indicates difference absorbance obtained by subtracting an absorbance measurement at the secondary wavelength 690 nm from an absorbance measurement at the primary wavelength 492 nm and the abscissa indicates the concentration of human annexin-V, in which each □ mark represents the average difference absorbance and the length of the arrows extending upward or downward from each □ mark represents the average ±2SD respectively.

Figure 10:

FIG. 10 is a microscopic photograph, under 200 diameter magnification, of human cardiac muscle tissue subjected to a specific staining by indirect enzyme antibody technique in which anti-human-annexin-V monoclonal antibody HCA-627 was employed as the primary antibody and HRPO-labeled-anti-mouse-immunoglobulin antibody was employed as the secondary antibody. The figure demonstrates that human annexin-V was stained in the form of uneven aggregates in the cytoplasm within the human heart of a patient with sudden death.

Figure 11:
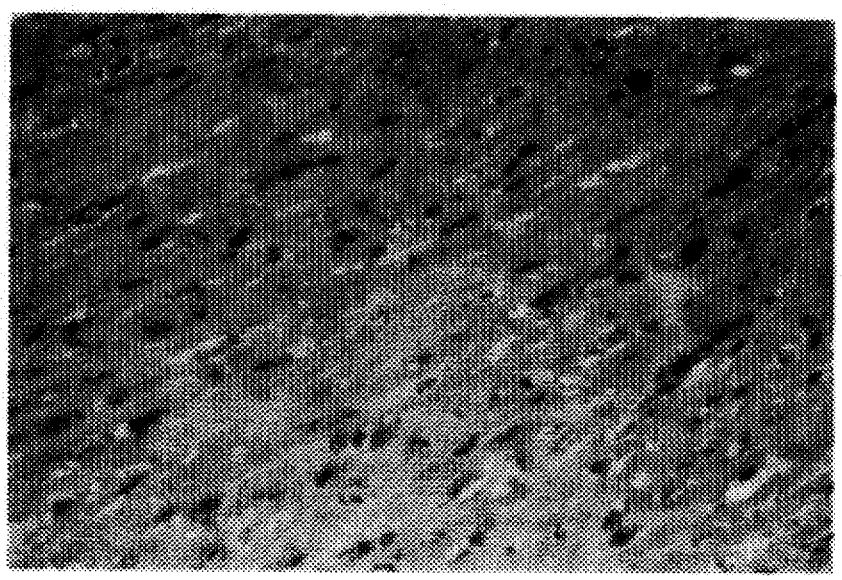

FIG. 11 is a microscopic photograph, under a 200 diameter magnification, of human cardiac muscle tissue for comparison with the example as shown by FIG. 10. The figure demonstrates that without the use of the anti-human-annexin-V monoclonal antibody, it is impossible to stain human annexin-V and therefore to locate the distribution thereof.

Figure 12:
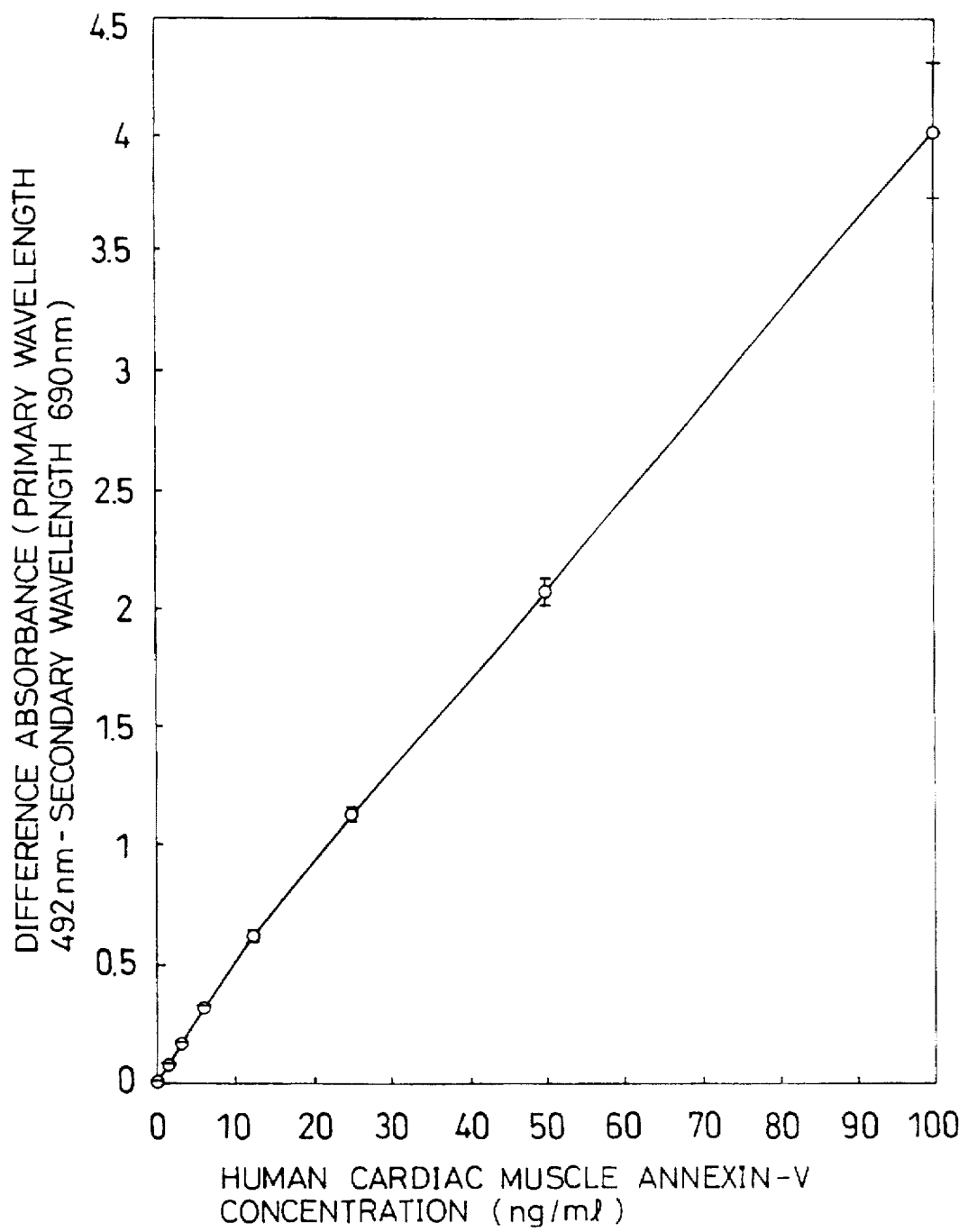

FIG. 12 illustrates a calibration curve for use in ELISA system for a working example, in which the anti-human-annexin-V monoclonal antibodies of the present invention are employed to determine the concentration of native human annexin-V. The ELISA system is made up of a combination of a HRPO-labeled anti-annexin-V monoclonal antibody, produced by HDA-907, an anti-annexin-V monoclonal antibody-producing hybridoma cell line clone, deposited under the number FERM BP-5286 at the International Depositary Authority for the deposit of microorganisms and having a specific activity with native human annexin-V, and another anti-human annexin-V monoclonal antibody as the solid-phase, produced by HCA-627, an anti-human-annexin-V monoclonal antibody-producing hybridoma cell line clone and having a specific activity with native human annexin-V.

In the Figure, the ordinate indicates absorbance obtained by subtracting an absorbance measurement at the secondary wavelength 690 nm from an absorbance measurement at the primary wavelength 492 nm and the abscissa indicates the concentration of human annexin-V, in which each ○ mark represents the average difference absorbance measured four times and the length of the arrows extending upward or downward from each ○ mark represents the average ±2SD respectively.

Figure 13:
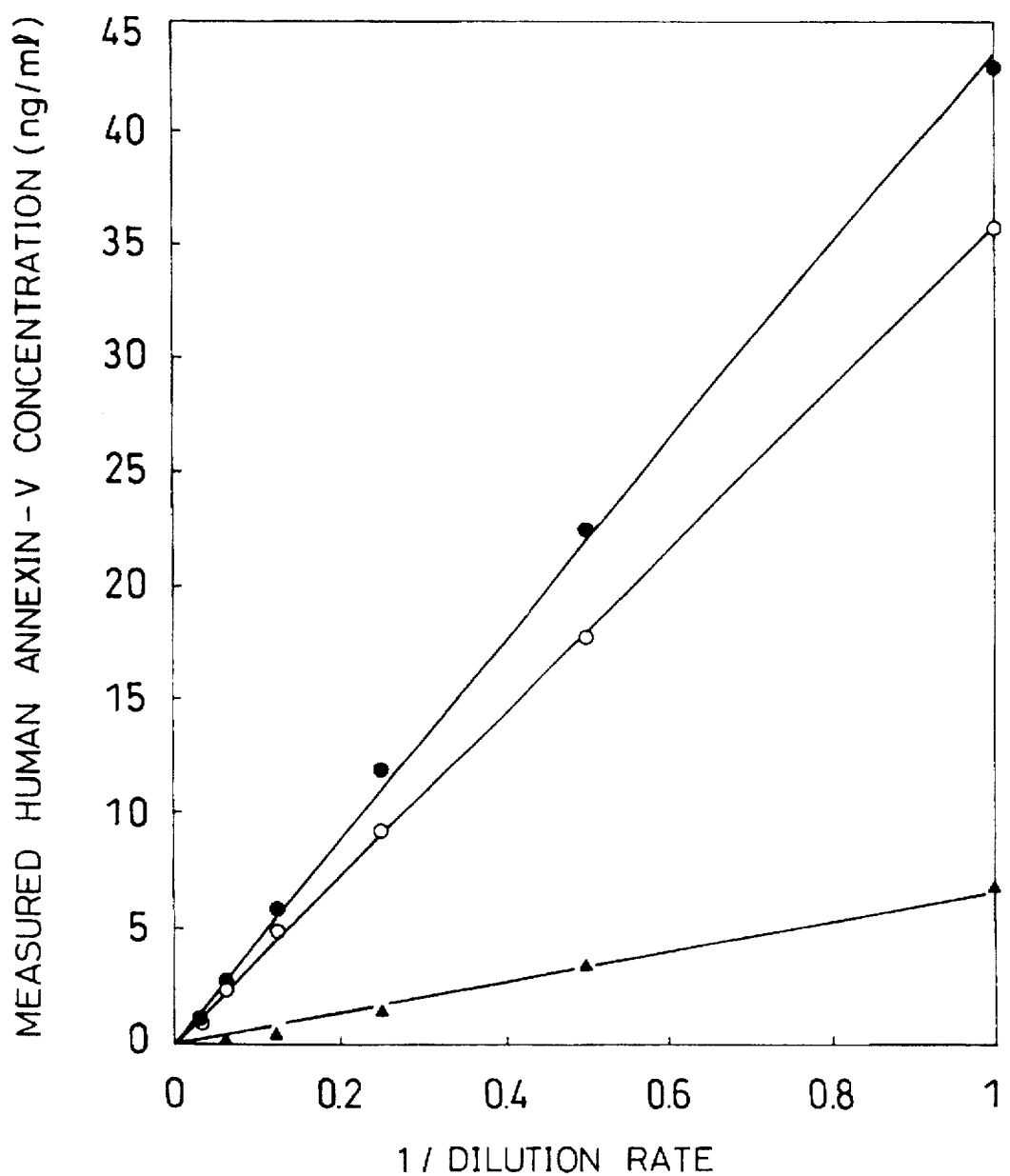

FIG. 13 shows the results of dilution tests performed on plasma samples by an ELISA system for assay of native human annexin-V concentration using the anti-annexin-V monoclonal antibodies of the present invention. The ELISA system was constructed using a combination of HRPO-labeled anti-human-annexin-V monoclonal antibody produced by anti-annexin-V monoclonal antibody-producing hybridoma cell line clone HDA-907 (deposited under the number FERM BP-5286 at the International Depositary Authority for deposit of microorganism) and having a specific reactivity with annexin-V and anti-human-annexin-V monoclonal antibody as solid phase produced by anti-annexin-V monoclonal antibody-producing hybridoma cell line clone HCA-627 (deposited under the number FERM BP-5284 at the International Depositary Authority for deposit of microorganism) and having a specific reactivity with native human annexin-V.

In the Figure, the ordinate shows human annexin-V concentration measured on the original solution and the series of diluted solution of each sample and the abscissa represents 1/dilution rate for each sample.

THE BEST MODE FOR CARRYING OUT THE INVENTION

While the present invention will be further illustrated by the examples given below, the invention is not to be limited by the following examples and description.

In the following examples the symbol M represents molarity and it indicates, for a solution of mixture, the mol per liter of the solution.

EXAMPLE 1

Hybridoma Preparation (1) Purification of Human Annexin-V

The heart was excised from a human adult cadaver. After clearing the blood, the right ventricle was excised from the heart, followed by the removal of the connective tissue and the lipids therefrom. These operations were carried out in ice or at a 4° C. temperature.

The heart was added with a buffer solution of the following composition in a ratio of ten times as much of the heart weight: 250 mM, sucrose 0.5 mM ethylene glycol bis(2-aminoethyl ether) tetraacetate (EGTA), 1 mM phenylmethane sulfonyl fluoride (PMSF) and 10 mM tris (tris (hydroxymethyl) aminomethane)HCl, pH7.4.

The heart was then homogenized by a homogenizer and the homogenate was centrifuged at 3000 xg for 15 minutes.

The separated supernatant is added with 1M $CaCl_2$ solution to give a final concentration of 2 mM for mixing, followed by centrifugation at 28,000 xg for an hour. To the residue was added 2 ml of 10 mM EGTA for suspending the residue. The residue suspension was centrifuged at 28,000 xg for 1 hour.

The supernatant was subjected to gel filtration with Sephacryl S-300 (trade name) column available from Pharmacia Co. for elution with pH 7.4 buffer solution (B) containing 0.1M NaCl and 30 mM Tris-HCl. The fraction containing protein having a molecular weight of 35 KDa was recovered and passed through an ion-exchange column (Biogelagarose: trade name) with an eluent of 10 mM Tris HCl solution (pH 7.4) containing NaCl in the concentration range of 0 to 0.3M for purification by means of NaCl-concentration-gradient elution.

The human annexin-V thus purified was divided into two portions, one of which was freeze-dried and then dissolved by 0.1M sodium phosphate buffer (pH 7.6) containing 8M urea. The other part was freeze-dried and dissolved by 0.1M sodium phosphate buffer (pH 7.6). The two parts were both preserved at 4° C. These parts of purified human annexin-V were measured for purity with sodium dodecyl sulfate polyacrylamide gel electrophoresis (SDS-PAGE) to quantify the protein concentration.

Identification was also made of the purified annexin-V protein: Peptide fractions were prepared by adding lysylendopeptidase and keeping the mixture at 37° C. for 15 hours so as to allow the human annexin-V protein to react with lysylendopeptidase. The peptides thus obtained were analyzed for amino acid sequence on a Shimadzu PPSQ-10 protein sequencer to determine the amino acid sequences of the two peptide fractions, based on Edman method (cf. Edman P. "A method for the determination of the amino acid sequence in peptide", Arch. Biochem. Biophys., 1949, Vol.22, page 475).

As the N-terminal amino acid sequences of the two peptides from the purified protein are Glu-Tyr-Gly-Ser-Ser-Leu-Glu (SEQ ID NO:1) for the first and Gly-Thr-Asp-Glu-Glu-Lys-Phe-Ile-Thr-Ile-Phe-Gly-Thr (SEQ ID NO:2) for the second, the protein was identified as annexin-V.

(2) Mice

BALB/c inbred-strain female mice 5 to 8 weeks of age were maintained on a diet of standard pellets feeding water ad libitum in an animal-breeding chamber kept at the temperature of 23°+1° C. and the humidity of 70%.

(3) Immunization

The human annexin-V 100 micrograms/0.5 ml as prepared in (1) was mixed with an equal amount of Freund's complete adjuvant to be emulsified. The human annexin-V in emulsion was administered as the antigen into the abdominal cavities of four female mice 5 weeks of age in a dose of 15–40 micrograms of the purified annexin-V per mouse. The administration was made every two weeks for two months for the immunization of the mice. The mice were determined for the antibody titer to select mice having a high titer, which were administered, three weeks after, with 50 micrograms of the purified human annexin-V as a booster intravenously through the mice tails for final immunization.

(4) Cell Fusion

Three days after final immunization, the spleens were excised from BALB/c mice and the spleen cells were suspended in EMEM culture medium to prepare a suspension of spleen cells. The spleen cells were then washed four times with EMEM medium (available from Nissui Co.) and determined for the number of cells. The result was that $7 \times 10^8$ living spleen cells were obtained.

Cell fusion was conducted using P3-X63-Ag8 653 culture cells, hereinafter referred to as X63 cells, as parent cell strain, which are 2-amino-6-oxy-8-azapuraine (8-azaguanine)-resistant and derived from BALB/c mouse myeloma. X63 cells in the logarithmic growth phase were employed to subculture in RPMI-1640 medium (at a concentration of 20 micrograms/ml and with 8-azaguanine) (available from GIBCO Co.), containing 10% of immobilized fetal calf serum (hereinafter referred to as FCS) available from Intergen Co. Further cultivation was conducted, from three days prior to the cell fusion, in RPMI-1640 medium containing 10% of FCS but not containing 8-azaguanine, in which the cells in the logarithmic growth phase were also employed. Following washing with RPMI-1640 medium three times, X63 cells were determined for the number of cells, with the result that the number of living X63 cells was $7 \times 10^7$.

Polyethylene glycol-4000 available from Sigma Co. was dissolved in RPMI-1640 medium to give a concentration of 50% (w/v) for use in the cell fusion.

The spleen cells and X63 cells were mixed in a ratio of the spleen cells: X63 cells=10:1. The mixture was centrifuged at 1500 rpm for five minutes, the supernatant was removed and the cells were well disintegrated to be used in the cell fusion. The cell fusion was carried out, using polyethylene glycol prepared in the aforesaid manner and kept at 37° C., in accordance with the method described in "Köhller and Milstein: Nature, Vol.256, pages 495–497 (1975)" and "European Journal of Immunology, Vol.6, pages 511–519 (1976)".

The cell lines following the cell fusion for the hybridoma formation were suspended in HAT selection medium containing RPMI-1640 added with FCS of a 10% concentration, $1 \times 10^{-4}$M hypoxanthine, $4 \times 10^{-7}$M aminopterine and $1.6 \times 10^{-5}$M thymidine, to give a spleen cell concentration of $2.0 \times 10^6$ per ml. Each 50 microliters aliquot of the cell suspension was distributed in 96 wells, and incubated an incubator kept at 37° C. temperature and 95% humidity under a 8% $CO_2$ atmosphere. One drop of the HAT medium was added to each well on the first day and the second day from the start of the incubation, followed by the addition of two drops of the same medium on the seventh and ninth day from the start for further incubation. Then incubation was carried out in a HAT-free culture medium. Approx. ten days to two weeks after the start, screening was made for hybridoma cell clones producing anti-human-annexin-V monoclonal antibodies capable of specifically reacting with human annexin-V treated with urea of 8M concentration (8M-urea-treated human annexin-V) and/or with human annexin-V not treated with 8M urea (native human annexin-V). The screening was done by ELISA using a human annexin-V absorption test and microplates in which human annexin-V as the antigenic protein is adsorved onto a solid phase.

All the clones of established hybridoma cell lines producing anti-human-annexin-V monoclonal antibodies as well as anti-dog-32KP polyclonal antibody are sensitized for solid phase. In addition, the anti-human-annexin-V monoclonal antibodies produced from such clones as well as anti-dog-32KP polyclonal antibody are labeled with biotin. Thus, a variety of ELISA methods were employed: the solid-phase-coupled clones and anti-dog-32KP polyclonal antibody are used in combination with the biotin-labeled anti-human-annexin-V monoclonal antibodies and also antidog-32KP polyclonal antibody, in order to detect clone(s) producing anti-human-annexin-V monoclonal antibodies which will specifically react with 8M-urea-treated human annexin-V, native human annexin-V and native human annexin-V in the human blood, serum or plasma not treated with 8M urea.

(5) Screening

As cell clones appeared ten days after the start of incubation, an absorption test with human annexin-V as the antigen was carried out by ELISA for the supernatants of hybridoma cell lines.

It was found by the present inventors that the antigenic activity of human annexin-V treated with 8M urea solution is significantly higher than that of native human annexin-V, with anti-32KP polyclonal antibodies described later. Thus, the human annexin-V absorption test was carried out using the two types of antigens: human annexin-V treated with 8M urea (hereinafter referred to as (8M-urea-treated human annexin-V) and human annexin-V with no such urea-treatment (hereinafter referred to as native human annexin-V).

Thus, a first set is constituted of 50 microliters per well of 8M-urea-treated human annexin-V solution (the 8M-urea-treated human annexin-V concentration being 200 ng/ml) and 50 microliters per well of the culture supernatant of hybridoma cell line distributed each U-bottomed well of a microtiterplate, while a second set is constituted of 50 microliters per well of native human annexin-V (the native human annexin-V concentration being 200 ng/ml) and 50 microliters per well of the supernatant of hybridoma cell line distributed in each U-bottomed well of another microtiterplate. Each well was added with 50 microliters of 20% suspension of Sepharose 4B combined with anti-mouse-immunoglobulin antibody and allowed to stand for 10 minutes following stirring for one hour. With each set, when it was observed that the anti-mouse-immunoglobulin antibody-combined Sepharose 4B completely sedimented on the well bottom, the respective supernatants 25 microliters were employed to measure remaining human annexin-V concentration therein by means of the human annexin-V ELISA method.

In this measurement, if any anti-human-annexin-V monoclonal antibodies against human annexin-V was present in the culture supernatant of hybridoma cell line, reactions will occur between human annexin-V and the anti-human-annexin-V monoclonal antibodies, followed by a reaction with anti-mouse-immunoglobulin monoclonal antibody-combined Sepharose 4B, resulting in the formation of antigen-antibody complexes which are to sediment. This will lead to a decrease in the human annexin-V content remaining in the supernatant and it is therefore possible to identify the presence of any anti-human-annexin-V monoclonal antibodies through the measurement of the human annexin-V concentration in the supernatant.

After the screening was completed in the above-mentioned manner for anti-human-annexin-V monoclonal antibodies capable of reacting with human annexin-V as the antigenic protein, a test was conducted to study the difference in epitopes with which the anti-human-annexin-V monoclonal antibodies will react.

Thus, 8M-urea-treated human annexin-V and native annexin-V as the antigenic solutions, each having been prepared to have a concentration of 1 microgram/ml, were absorbed onto a microtiterplate in an amount of 50 microliters per well, followed by washing three times with phosphate buffer solution (hereinafter referred to as PBS) containing 0.05% Tween-20, a Tween surfactant, and blocking with PBS containing 1% BSA to prepare plates with solid phase-coupled human annexin-V antigens.

A solid phase-coupled human annexin-V antigen in the plates thus obtained was allowed to react, for one hour at room temperature, with a culture supernatant of the hybridoma cell lines producing monoclonal antibodies capable of reacting with human annexin-V screened by the human annexin-V absorption test. The resulting antigen-antibody complexes were subjected to three times of washing with the washing solution and allowed to react, for thirty minutes at room temperature, with anti-mouse-immunoglobulin antibodies (from goats) labeled with horseradish peroxidase (hereinafter referred to as HRPO). Following the reaction, the resultant antigen-antibody complexes were subjected to washing four times with the washing solution and allowed to react, at room temperature for five minutes, with OPD substrate solution containing 0.1M phosphate-citrate buffer solution, 2 mg/ml o-phenylenediamine and 4 mM $H_2O_2$, and then the reaction was terminated with 2N $H_2SO_4$ and absorbance measurement was performed by the dual wavelength method at 492 nm as the primary wavelength and at 690 nm as the secondary wavelength on an ELISA plate reader.

At the primary wavelength 492 nm absorbance is measured with the substrate undergone the reaction due to the bound labeled-antibodies, while at the secondary wavelength the absorbance reflects cracks or stains of the microtiterplates. Accordingly, the subtraction of the absorbance at the secondary wavelength from that at the primary wavelength makes it possible to determine the absorbance reflecting the amount of the enzyme on the labeled antibodies which have bound to the solid phase-coupled antigen in proportion to the amount of the antigen.

(6) Studies on Reactivities with Solid Phases Sensitized with Annexin-V Antigens from Various Organs and Animals Studies were made of the anti-human-annexin-V monoclonal antibodies thus obtained for the species-dependent specificities with annexin-V derived from various human organs and animals, using the solid phases sensitized in the above-mentioned manner for human annexin-V.

With each annexin purified from the various human organs and animals, a solution was prepared to give a concentration of 1 microgram/ml with 0.1M phosphate buffer at pH 7.5. 50 microliters of each antigen solution was distributed in a 96-well microtiterplate for the adsorption overnight at 4° C., followed by washing twice with the washing solution and blocking with the blocking solution. The solid phases sensitized with the various annexin-V antigens were allowed to react with the anti-human-annexin-V monoclonal antibodies obtained by the example herein. The reaction products were assayed by the ELISA method in the same manner for the screening, for determining the reactivities of the anti-human-annexin-V monoclonal antibodies as obtained by the present invention with the respective annexin-V antigens.

(7) Studies on Reaction Specificities by Western Blotting

Homogenized specimens of the human cardiac muscle, the human liver, the human kidney, the human lungs, the beagle's cardiac muscle and the rat's cardiac muscle were subjected to sodium dodecyl sulfate-polyacrylamide gel electrophoresis (SDS-PAGE) using 10 to 20% polyacrylamide gel to fractionate the protein fractions. The protein fractions are then transferred into nitrocellulose membranes, followed by a blocking with PBS containing 3% skim milk and 1% BSA. Then the protein fractions fixed onto the membranes were allowed to react with the respective monoclonal antibodies to examine reactive protein fractions derived from the various organs and animals.

(8) Establishment of Hybridoma Cell Lines Producing Monoclonal Antibodies

Based on the above-mentioned studies, eighty-four strains were screened which are hybridoma cell line clones capable of reacting with 8M-urea-treated human annexin-V, through the absorption test using human cardiac muscle annexin-V. From such strains twenty-one clone strains were strictly selected depending upon the difference in reactivities with type of annexin-V derived from the various organs and animals. Thus, the twenty-one strains were classified into the following five groups depending upon the reactivities:

(i) Clones which exhibit a high reactivity in the 8M-urea-treated human cardiac muscle annexin-V absorption test, but do not exhibit reactivities with any of the antigen-sensitized solid phases: five strains (clone HCA-212, clone HCA-290, clone HCA-656, clone HCA-713 and clone HCA-805).

(ii) Clones which exhibit a high reactivity in the 8M-urea-treated human cardiac muscle annexin-V absorption test and also exhibit a high reactivity with the human-annexin-V-sensitized solid phase, but exhibit almost no or a low reactivity with the beagle dog- and rat-derived-annexin-V-sensitized solid phases: eight strains (clone HCA-69H, clone HCA-155H, clone HCA-231H, clone HCA-671H, clone HCA-770H, clone HCA-784H, clone HCA-803H and clone HCA-838H).

(iii) Clones which exhibit high reactivities in the 8M-urea-treated human cardiac muscle annexin-V absorption test, as well as with all of the solid phases sensitized with annexin-V antigens derived from the various human organs, the beagle's and the rat's cardiac muscles: four strains (clone HCA-57HDR, clone HCA-293HDR, clone HCA-350HDR and clone HCA-805HDR).

(iv) Clones which exhibit high reactivities in the 8M-urea-treated human cardiac muscle annexin-V absorption test and also with the solid phases sensitized with annexin-V antigens from the human cardiac muscle, the human kidney or the human liver, but exhibit only low reactivities with the solid phases sensitized with annexin-V antigens from the beagle's and the rat's cardiac muscles: three strains (clone HCA-507HD, clone HCA-660HD and clone HCA-646HD).

(v) A clone which exhibit high reactivities in the 8M-urea-treated human cardiac muscle annexin-V absorption test as well as in the native human cardiac muscle annexin-V absorption test: one strain (clone HCA-627).

Thus, there were obtained monoclonal antibodies having different reactivities as classified into the five groups mentioned in the above.

The reaction specificities of these monoclonal antibodies are shown in Table 1 below.

TABLE 1

Reaction Specificities of Anti-human-cardiac-muscle-annexin-V Monoclonal Antibodies
(Absorbance = A4902 nm 690 nm)

| Cell fusion No. 1 Anti-human-cardiac-muscle annexin-V Mab clone No. | Mouse Immunogulobulin Isotype | | Absorption Rate (%) in 8M-urea-treated Human-cardiac-muscle Annexin-V Absorption Test | Absorption Rate (%) in Native Human cardiac-muscle Annexin-V Antigen Absorption Test | Absorption Rate (%) in 8M-urea-treated Dog Annexin-V Antigen Absorption Test |
|---|---|---|---|---|---|
| | H-chain | L-chain | | | |
| HCA-212 | IgG1 | k | 85 | 40 | 64 |
| HCA-290 | IgG1 | k | 82 | 10 | 86 |
| HCA-656 | IgG1 | k | 67 | 1 | 57 |
| HCA-713 | IgG2a | k | 47 | 4 | 29 |
| HCA-805 | IgG1 | k | 83 | 38 | 55 |
| HCA-69H | IgG2b | k | 87 | 3 | 4 |
| HCA-155H | IgG2a | k | 89 | 18 | 31 |
| HCA-231H | IgG2a | k | 90 | 6 | 24 |
| HCA-671H | IgG2a | k | 91 | 9 | 29 |
| HCA-770H | IgG2b | k | 88 | 7 | 26 |
| HCA-784H | IgG2a | k | 88 | 3 | 26 |
| HCA-803H | IgG2a | k | 88 | 5 | 20 |
| HCA-838H | IgG2a | k | 88 | 6 | 10 |
| HCA-507HD | IgG2a | k | 90 | 7 | 36 |
| HCA-660HD | IgG1 | k | 90 | 9 | 42 |
| HCA-646HD | IgG2b | k | 91 | 5 | 35 |
| HCA-57HDR | IgG2a | k | 62 | 7 | 46 |
| HCA-293HDR | IgG2a | k | 66 | 5 | 55 |
| HCA-350DHR | IgG2a | k | 65 | 3 | 52 |
| HCA-805HDR | IgG1 | k | 57 | 4 | 45 |
| HCA-627 | IgG1 | k | 99 | 99 | 87 |
| reagent blank | | | 0 | 0 | 0 |

| Reactivity with Solid-phase of Human Cardiac Muscle-derived Annexin-V Antigen (1 μg/ml Antigen sensitized at 50 μl/well) | | Reactivity with Solid-phase of Human Kidney-derived Annexin-V Antigen (1 μg/ml Antigen sensitized at 50 μl/well) | | Reactivity with Solid-phase of Human Liver-derived Annexin-V Antigen (1 μg/ml Antigen sensitized at 50 μl/well) | |
|---|---|---|---|---|---|
| Absorbance in 8M-urea-treated Antigen Sensitization | Absorbance in Native Antigen Sensitization | Absorbance in 8M-urea-treated Antigen Sensitization | Absorbance in Native Antigen Sensitization | Absorbance in 8M-urea-treated Antigen | Absorbance in Native Antigen Sensitization |
| 0.009 | 0.079 | 0.009 | 0.026 | 0.033 | 0.011 |
| 0.145 | 0.080 | 0.018 | 0.026 | 0.045 | 0.008 |
| 0.119 | 0.131 | 0.012 | 0.040 | 0.109 | 0.010 |
| 0.023 | 0.080 | 0.015 | 0.006 | 0.007 | 0.005 |

TABLE 1-continued

Reaction Specificities of Anti-human-cardiac-muscle-annexin-V Monoclonal Antibodies
(Absorbance = A4902 nm 690 nm)

| | | | | | |
|---|---|---|---|---|---|
| 0.014 | 0.096 | 0.010 | 0.021 | 0.029 | 0.006 |
| 9.460 | 13.240 | 4.610 | 4.420 | 1.191 | 2.712 |
| 11.330 | 14.650 | 6.670 | 7.520 | 2.074 | 4.690 |
| 9.230 | 14.260 | 5.110 | 5.060 | 1.529 | 3.160 |
| 8.900 | 15.680 | 6.950 | 7.850 | 2.421 | 5.620 |
| 11.260 | 12.030 | 3.680 | 3.560 | 1.077 | 2.268 |
| 9.860 | 14.080 | 5.580 | 5.860 | 1.854 | 4.210 |
| 12.730 | 14.440 | 5.890 | 6.580 | 2.269 | 5.270 |
| 10.450 | 13.860 | 4.630 | 5.000 | 1.508 | 3.190 |
| 10.110 | 15.940 | 7.420 | 8.840 | 3.090 | 6.710 |
| 13.540 | 15.170 | 7.300 | 8.930 | 3.300 | 6.340 |
| 8.360 | 13.240 | 5.530 | 6.390 | 1.986 | 4.190 |
| 9.910 | 8.140 | 2.459 | 1.465 | 0.531 | 0.464 |
| 12.330 | 12.590 | 3.740 | 3.290 | 0.923 | 1.156 |
| 12.510 | 9.190 | 3.180 | 2.305 | 0.729 | 0.853 |
| 2.499 | 0.766 | 0.096 | 0.063 | 0.048 | 0.051 |
| 0.042 | 0.224 | 0.036 | 0.066 | 0.193 | 0.015 |
| 0.041 | 0.045 | 0.014 | 0.015 | 0.009 | 0.010 |

| Reactivity with Solid-phase of Rat Cardiac Muscle-derived Annexin-V Antigen (1 μg/ml Antigen Sensitized at 50 μl/well) | | Reactivity with Solid-phase of Beagle Cardiac Muscle-derived Annexin-V Antigen (1 μg/ml Antigen Sensitized at 50 μl/well) | |
|---|---|---|---|
| Absorbance in 8M-urea-treated Antigen Sensitization | Absorbance in Native Antigen Sensitization | Absorbance in 8M-urea-treated Antigen Sensitization | Absorbance in Native Antigen Sensitization |
| 0.008 | 0.006 | 0.016 | 0.020 |
| 0.043 | 0.080 | 0.126 | 0.670 |
| 0.367 | 0.371 | 0.318 | 1.664 |
| 0.031 | 0.014 | 0.017 | 0.127 |
| 0.005 | 0.005 | 0.021 | 0.030 |
| 0.011 | 0.011 | 0.006 | 0.002 |
| 0.143 | 0.183 | 0.010 | 0.009 |
| 0.057 | 0.056 | 0.011 | 0.009 |
| 0.204 | 0.217 | 0.011 | 0.013 |
| 0.033 | 0.040 | 0.009 | 0.014 |
| 0.064 | 0.062 | 0.008 | 0.009 |
| 0.105 | 0.118 | 0.004 | 0.005 |
| 0.014 | 0.016 | 0.011 | 0.007 |
| 0.489 | 0.524 | 0.008 | 0.044 |
| 0.507 | 0.594 | 0.017 | 0.061 |
| 0.279 | 0.318 | 0.013 | 0.028 |
| 5.360 | 6.110 | 13.060 | 18.590 |
| 9.820 | 11.190 | 15.620 | 19.340 |
| 7.500 | 9.280 | 14.620 | 19.020 |
| 1.292 | 1.855 | 3.820 | 14.400 |
| 0.146 | 0.179 | 0.440 | 3.070 |
| 0.006 | 0.006 | 0.008 | 0.008 |

(9) Cloning

The hybridoma cell lines producing monoclonal antibodies as classified into the above-mentioned five groups were subjected to cloning by the limiting dilution to obtain a single clone. In performing the cloning, thymus cells prepared from BALB/c mice and suspended in HAT medium was added as the feeder cell at a rate of $1 \times 10^6$ per well.

(10) Identification of Mouse Immunoglobulin Subclass

Identification of mouse immunoglobulin subclass was made with the monoclonal antibodies produced by the hybridoma cell lines which have been prepared as having a single clone by means of the above-mentioned cloning. The culture supernatants of the respective hybridoma cell lines were assayed for the mouse immunoglobulin subclass identification using a MONOAb typing kit (available from Zymed Co.)

The result was that seven clones have IgG1 type, eleven clones IgG2a type and three clones IgG2b type, with regard to the H chain. Regarding the L chain, all the clones were found to have k chain (Table 1).

The respective clones classified into the five groups are shown in Table 1.

EXAMPLE 2

Production of Monoclonal Antibodies (1) Harvest of Ascitic Fluid

In order to obtain a higher concentration of anti-human-cardiac-muscle-annexin-V monoclonal antibodies, the various hybridoma cells are grown and the resulting respective clones were inoculated, following washing three times with EMEM culture solution, into the ascitic cavities of BALB/c mice which have been administered with 2,6,10,14-tetramethyl pentadecane (pristane) in advance into their ascitic cavities. The ascitic fluids were harvested seven to fourteen days after the inoculation of the hybridoma cell lines into the ascitic cavities. The ascitic fluids thus obtained were applied to centrifuge to remove the cellular and residual fractions. The supernatant fractions were pooled for keeping at 4° C.

(2) Purification for the Anti-Human Cardiac-Muscle-Annexin-V Monoclonal Antibodies from the Ascitic Fluids The respective anti-human-cardiac-muscle-annexin-V monoclonal antibodies were purified by a combination of salting-out and ion-exchange chromatography to recover the purified IgG fractions.

Thus, 20 ml of each clone was added with an equal amount of phosphate-buffered saline (PBS), followed by the addition of anhydrous sodium sulfate to give a final concentration of 20%(w/v) with stirring at room temperature. The mixture was stirred for an additional one hour.

Centrifugation was then performed at 12,000 rpm with a high-speed centrifuge (available form Hitachi. Co.) and the resulting residue fraction was dissolved in approx. 10 ml of phosphate-buffered saline. The solution was dialyzed three times against 20 mM sodium phosphate buffer solution (pH 7.0) as the outer solution. On completing the dialysis, from the dialyzed solution the IgG fraction of the anti-human-cardiac-muscle-annexin-V monoclonal antibody was purified by ion-exchange chromatography using a DEAE (diethylaminoethyl cellulose) column DE-52 (available from Whatman Co.) measuring 1.5 cm in inner diameter and 8 cm in length equilibrated with 20 mM sodium phosphate buffer solution (pH 7.0), from which the purified IgG fraction was obtained as the pass-through fraction or as the eluent fraction at a NaCl concentration in the range of 30 mM gradationally up to 50 mM formed with 20 mM sodium phosphate buffer solution (pH 7.0) containing 30 mM to 50 mM NaCl. Each of the purified clones was determined for the purity of IgG fraction, by high performance liquid chromatography using a TSK gel G3000SW column (available from Tosoh. Co.) and sodium dodecyl sulfate-polyacrylamide gel electrophoresis (SDS-PAGE) using PhastSystem available from Pharmacia Co. The purity was found to be 95% or higher.

EXAMPLE 3

ELISA Assay System for Human Cardiac Muscle Annexin-V (1) Preparation of Anti-Human-Cardiac-Muscle-Annexin-V Monoclonal Antibodies for HRPO-Labeling The IgG fractions of clones HCA-155 and HCA-660HD were purified in the manner as described in Example 2 to study the application to ELISA system for human cardiac muscle annexin-V assay.

(2) Preparation of HRPO-Labeled Anti-Human-Cardiac-Muscle-Annexin-V Monoclonal Antibodies (A) Preparation of Anti-Human-Cardiac-Muscle-Annexin-V Monoclonal Antibodies F(ab')$_2$ For labeling the IgG fractions of the anti-human-cardiac-muscle-annexin-V monoclonal antibodies, each 10 mg of the anti-human-cardiac-muscle-annexin-V monoclonal antibodies was subjected to centrifugal filtration with a centrifugal concentrator (Centricon 10 available from Amicon Co.), to give a final volume of 1 ml. The concentrated antibody was dialyzed against 0.1M sodium acetate buffer (pH 4.0) containing 0.2M NaCl as the solvent.

The IgG solution resulting from the dialysis was added with a solution of pepsin (available from Sigma Co.) dissolved in 1M sodium acetate buffer (pH 4.0) containing 0.2M NaCl, so that the pepsin is 4% of the IgG content, followed by reaction at 37° C. for 6 to 16 hours. On completing the reaction, the resultant was applied to molecular-sieve chromatography using a Sephadex G-150 column (available from Pharmacia Co.) for gel filtration, which has been equilibrated with 0.1M sodium borate buffer (pH 8.0), to obtain the F(ab')$_2$ fragments of the respective anti-human-cardiac-muscle-annexin-V monoclonal antibodies.

(B) Preparation of Anti-Human-Cardiac-Muscle-Annexin-V Monoclonal Fab'-SH

Each of the anti-human-cardiac-muscle-annexin-V monoclonal antibodies F(ab')$_2$ as prepared in the aforesaid (A) was subjected to centrifugation for further concentration by a Centricon centrifugal concentrator to prepare the concentrated F(ab')$_2$ fractions of the respective anti-human-cardiac-muscle-annexin-V monoclonal antibodies.

The concentrated fraction was added with 0.1 ml of 100 mM 2-mercaptoethylamine hydrochloride (available from Kishida Chemicals Co.) solution for reaction at 37° C. for 90 minutes. On completing the reaction, the resultant was applied to a Sephadex G-25 column for equilibrium gel filtration (available from Pharmacia Co.) measuring 1.6 cm in diameter and 20 cm in length which has been equilibrated with 0.1M sodium phosphate buffer (pH 6.0) containing 1 mM EDTA, for fractional purification of the Fab'-SH fraction, followed by centrifugal concentration by a Centricon 10 centrifugal concentrator, to give a final volume of 1 ml. Thus, the concentrated Fab'-SH fractions of clones HCA-155H and HCA-660HD anti-human-cardiac-muscle-annexin-V monoclonal antibodies were prepared.

(C) Preparation of HRPO Maleimide

Ten mg (as a protein content) of HRPO (available from Boehlinger Co.) was dissolved in 1 ml of 0.1M sodium phosphate buffer (pH 6.0). The resulting solution was added with 100 microliters solution of N-hydroxysuccinimide ester (available from Zeeben Chemicals Co.) dissolved in dimethylformamide (DMF) (available from Kishida Chemicals Co.) to give a final concentration of 25 mg/ml, followed by reaction at 30° C. for 60 minutes to prepare maleimide ester of HRPO. On completing the reaction, the solution was centrifuged for five minutes at 3000 rpm. The supernatant was applied to a Sephadex G-25 column for equilbrium gel filtration (available from Pharmacia Co.) measuring 1.6 cm in diameter and 20 cm in length, which has been equilibrated with 0.1M sodium phosphate buffer (pH 6.0), in order to purify HRPO maleimide. The purified fraction of HRPO maleimide was then subjected to centrifugal concentration by a Centricon 10 centrifugal concentrator to prepare the concentrated fraction of HRPO maleimide.

(D) Preparation of HRPO-Labeled Anti-Human-Cardiac-Muscle-Annexin-V Monoclonal Fab' Antibodies The concentrated Fab'-SH fraction of each anti-human-cardiac-muscle-annexin-V monoclonal antibody and the concentrated fraction of HRPO maleimide were mixed together at a molar ratio of 1:1, for reaction at 4° C. for 15 to 24 hours. On completing the reaction, 2-mercaptoethylamine was added to give a concentration of 2 mM in the reaction solution, followed by reaction at 37° C. for 20 minutes in order to block unaltered HRPO maleimide. The resultant was then subjected to molecular-sieve gelchromatography using a Ultragel ACA44 column (available from Pharmacia Co.) equilibrated with 20 mM sodium phosphate—sodium citrate buffer containing 0.15M NaCl and 2.5 mM EDTA (pH 5.6) and measuring 1.6 cm in diameter and 65 cm in length, for removing unaltered Fab'-SH of the anti-human-cardiac-muscle-annexin-V monoclonal antibodies and unaltered HRPO maleimide and purifying the HRPO-labeled anti-human-cardiac-muscle-annexin-V monoclonal Fab' antibodies (hereinafter referred to as HRPO-labeled anti-human-cardiac-muscle-annexin-V monoclonal antibodies).

(3) Preparation of Anti-Dog-32KP Polyclonal Antibodies IgG

Anti-dog-32KP-annexin-V polyclonal antiserum was obtained by immunizing rabbits with dog-derived purified 32KP annexin-V antigen. To three ml of the antiserum was added an equal amount of phosphate-buffered saline (PBS), followed by the addition of anhydrous sodium sulfate to give a final concentration of 20% with stirring and an additional stirring for one hour at room temperature. The resultant was then centrifuged at 12,000 rpm for 10 minutes, and the residue obtained was dissolved in approx. 3 ml of saline. The solution was then subjected to dialysis against 20 mM sodium phosphate (pH 7.0) as the solvent. On completing the dialysis, the resulting solution was applied to ion-exchange chromatography using a DEAE cellulose DE-52 column (available from Whatman Co.) equilibrated with 20 mM sodium phosphate buffer (pH 7.0) and measuring 1.5 cm in diameter and 6 cm in length, to purify the IgG fraction of anti-dog-32KP-annexin-V polyclonal antibody. From 3 ml of the anti-dog-32KP-annexin-V polyclonal antibody-containing antiserum there was obtained 13 mg of the purified IgG fraction.

(4) Preparation of HRPO-Labeled Anti-Dog-32KP-Annexin-V Polyclonal Antibody (A) Preparation of Anti-Dog-32KP-Annexin-V Polyclonal Antibody F(ab')$_2$ For labeling the purified IgG fraction of the anti-dog-32KP-annexin-V polyclonal antibody, 12 mg of aforesaid antibody was applied to a Centricon 10 centrifugal concentrator (available from Amicon Co.) to give a concentrated volume of 1 ml, followed by dialysis against 0.1M sodium acetate buffer (pH 4.5) containing 0.2M NaCl.

The antibody solution resulting from the dialysis was added with a solution of pepsin (available from Sigma Co.) dissolved in 0.1M sodium acetate (pH 4.5) containing 0.2M NaCl to give a concentration of 4% based on the IgG content, followed by reaction at 37° C. for 16 hours. On completing the reaction, the resultant was applied to molecular-sieve chromatography using a Sephadex G-150 column for equilibrium gel filtration (available from Pharmacia Co.) equilibrated with 0.1M sodium borate buffer (pH 8.0) and measuring 1.6 cm in diameter and 65 cm in length, to fractionate and purify the F(ab')$_2$ fraction of the antibody. The resulting fraction was subjected to dialysis against sodium phosphate buffer (pH 6.0) containing 1 mM EDTA as the solvent. On completing dialysis, the dialyzed solution was applied to centrifugal concentration by a Centricon 10 centrifugal concentrator to give a final volume of 1 ml. The solution resulting from the dialysis was used to prepare the labeled antibody as the anti-dog-32KP-annexin-V F(ab')$_2$ polyclonal antibody. Thus, from 12 mg of the IgG fraction of the anti-dog-32KP polyclonal antibody obtained in the above-mentioned manner, there was prepared approx. 7 mg of the F(ab')$_2$ fraction.

(B) Preparation of Anti-Dog-32KP-Annexin-V Polyclonal Fab'-SH

To 7 mg/ml solution of anti-dog-32KP polyclonal antibody F(ab')$_2$ fraction as prepared in above (A) was added 0.1 ml of 100 mM 2-mercaptoethylamine chloride (available from Kishida Chemicals Co.) for reaction at 37° C. for 90 minutes. On completing the reaction, the resultant was applied to a Sephadex G-25 column (available fro Pharmacia Co.) for equilibrium gel filtration measuring 1.6 cm in diameter and 20 cm in length equilibrated with 0.1M sodium phosphate buffer (pH 6.0) containing 1 mM EDTA, to purify the Fab'-SH fraction. The fraction was then subjected to centrifugal concentration by a Centricon 10 centrifugal concentrator to a volume of 1 ml. Thus, from 7 mg of the F(ab')$_2$, there was obtained 6.1 mg of anti-dog32KP annexin-V polyclonal antibodies Fab'-SH.

(C) Preparation of HRPO Maleimide

Ten mg (as a protein content) of HRPO (available from Boehlinger CO.) was dissolved in 1 ml of 0.1M sodium phosphate buffer (pH 6.0). The resulting solution was added with 100 microliters solution of N-hydroxysuccinimide ester (available from Zeeben Chemicals Co.) dissolved in dimethylformamide (DMF) (available from Kishida Chemicals Co.) to give a final concentration of 25 mg/ml, followed by reaction at 30° C. for 60 minutes to prepare maleimide ester of HRPO. On completing the reaction, the solution was centrifuged for five minutes at 3000 rpm. The supernatant was applied to a Sephadex G-25 column for equilibrium gel filtration (available from Pharmacia Co.) measuring 1.6 cm in diameter and 20 cm in length, which has been equilibrated with 0.1M sodium phosphate buffer (pH 6.0), in order to purify HRPO maleimide. The purified fraction of HRPO maleimide was then subjected to (centrifugal) concentration by a Centricon 10 centrifugal concentrator to prepare the concentrated fraction of HRPO maleimide.

(D) Preparation of HRPO-Labeled Anti-Dog-32KP-Annexin-V Polyclonal Antibody Fab'

The Fab'-SH fraction of anti-dog-32KP-annexin-V polyclonal antibody thus obtained was mixed with the HRPO maleimide fraction at a molar ratio of 1:1, for reaction at 4° C. for 15 to 24 hours. Then the resultant was added with 2-mercaptoethylamine hydrochloride to give a concentration of 2 mM in the reaction solution, followed by reaction at 37° C. for 20 minutes to block unaltered HRPO maleimide. The resultant was then subjected to gelchromatography using a Ultrogel ACA44 column (available from Pharmacia Co.) equilibrated with 20 mM sodium phosphate-sodium citrate buffer (pH 5.6) containing 0.15M NaCl and 2.5 mM EDTA and measuring 1.6 cm in diameter and 65 cm in length, for removing unaltered anti-dog-32KP-annexin-V polyclonal antibody Fab'-SH fraction and unaltered HRPO maleimide and purifying HRPO-labeled anti-dog-32KP-annexin-V polyclonal antibody (hereinafter referred to as HRPO-labelled antibodies).

(E) HRPO Activity Determination

In determining the HRPO enzyme activity of the HRPO-labeled antibodies, 2.98 ml of 0.1M sodium phosphate buffer (pH 7.0) containing 0.2% phenol, 0.5 mM hydrogen peroxide and 0.15 mg/ml 4-amino antipyrine were added with 20 microliters of the HRPO-labeled antibodies to give a total volume of 3.0 ml, followed by reaction at 37° C. for five minutes, and measurement of absorbance at 500 nm by means of the Rate assay. HRPO activity was determined by measuring the difference in absorbance ($\Delta$Abs) per one minute.

(5) Preparation of Anti-Human-Cardiac-Muscle-Annexin-V Monoclonal Antibodies Solid Phase As monoclonal antibodies for use in the solid phase in an ELISA system for the assay of human cardiac muscle annexin-V clones HCA-290, HCA-627, HCA-57HDR, HCA-293HDR and HCA-350HDR were selected and the IgG fractions of the respective clones were purified from the ascitic fluids in the same manner described in Example 3.

The IgG fraction of each of the anti-human annexin-V monoclonal antibodies was adjusted to have a concentration of 30 micrograms/ml with 0.1M sodium phosphate buffer (pH 7.5) containing 0.1% sodium azide, and distributed in a microtiterplate for ELISA (available from Nunc Co.) at a rate of 100 microliters per well, for sensitization at 4° C. overnight. Then each well of the microtiterplate was washed three times with phosphate-buffered saline (PBS) containing 0.05% Tween 20 surfactant, and then added with 300 microliters of PBS containing 1% BSA (as the blocking solution), followed by a further blocking operation at 4° C. overnight, to prepare antibody-plates sensitized with anti-human-cardiac-muscle-annexin-V monoclonal antibodies (hereinafter referred to as anti-human-annexin-V monoclonal antibody plates).

(6) Studies on ELISA Assay System Using Anti-Human-Annexin-V Monoclonal Antibodies The anti-human-annexin-V monoclonal antibody plates prepared in the above-mentioned manner were added, after the blocking solution discarded, with 10 mM sodium phosphate buffer (pH 7.0) containing 1% BSA, 0.15M NaCl and 5 mM EDTA at a rate of 100 microliters per well. Standard antigen solutions were prepared, with 8M-urea-treated human annexin-V antigen (obtained by the treatment with 8M urea), and native annexin-V (obtained by no treatment with 8M urea), to give concentrations of 1.5625 ng/ml, 3.125 ng/ml, 6.25 ng/ml, 12.5 ng/ml, 25 ng/ml, 50 ng/ml and 100 ng/ml. The respective standard antigen solutions were added to the well at a rate of 20 microliters per well,
followed by stirring and reaction for one hour at room temperature. On completing the reaction, each well was washed three times with the washing solution. To each of the washed wells were added the HRPO-labeled anti-human-annexin-V monoclonal antibodies Fab' (from clones HCA-155H and HCA-660HD) at a rate of 100 microliters per well, for reaction at room temperature for thirty minutes. Following the reaction, each well was washed six times with washing solution and then added with 100 microliters of OPD substrate solution containing 2 mg/ml o-phenylenediamine and 4 mM $H_2O_2$, for reaction for thirty minutes. The reaction was terminated by adding 2N $H_2SO_4$ solution at a rate of 100 microliters per well. Absorbance was determined on an ELISA plate reader by the dual wavelength method at 492 nm as the primary and at 690 nm as the secondary.

The absorbance herein intended is obtained by subtracting an absorbance measurement at the secondary wavelength 690 nm from that at the primary wavelength 492 nm.

The results of the absorbance measured are given in Table 2 below, with respect to 8M-urea-treated-human annexin-V standard antigen solutions.

TABLE 2-1

Assay of 8M-urea-treated Human Annexin-V Antigen by Monoclonal Antibodies ELISA System
Combination of Monoclonal Antibodies for ELISA System: HRPO-labeled-HCA-155H Antibody and HCA-290 Solid Phase (Absorbance A492 nm – 690 nm)

| Concentration of 8M-urea-treated Human Annexin-V Antigen (ng/ml) | Number of Measurements | | | Standard Deviation (SD) | Average –2SD | Average | Average +2SD |
|---|---|---|---|---|---|---|---|
| | 1 | 2 | 3 | | | | |
| 0 | 0.006 | 0.010 | 0.080 | 0.042 | –0.051 | 0.032 | 0.115 |
| 1.5625 | 0.043 | 0.048 | 0.041 | 0.004 | 0.037 | 0.044 | 0.051 |
| 3.125 | 0.093 | 0.090 | 0.084 | 0.005 | 0.080 | 0.089 | 0.098 |
| 6.25 | 0.192 | 0.160 | 0.195 | 0.009 | 0.144 | 0.182 | 0.221 |
| 12.5 | 0.352 | 0.340 | 0.357 | 0.009 | 0.332 | 0.350 | 0.367 |
| 25 | 0.738 | 0.736 | 0.726 | 0.006 | 0.720 | 0.733 | 0.746 |
| 50 | 1.582 | 1.618 | 1.615 | 0.020 | 1.565 | 1.605 | 1.645 |
| 100 | 2.990 | 2.894 | 2.892 | 0.056 | 2.813 | 2.925 | 3.037 |

TABLE 2-2

Assay of 8M-urea-treated Human Annexin-V Antigen by Monoclonal Antibodies ELISA System
Combination of Monoclonal Antibodies for ELISA System: HRPO-labeled-HCA-155H Antibody and HCA-57HDR Solid Phase (Absorbance A492 nm – 690 nm)

| Concentration of 8M-urea-treated Human Annexin-V Antigen (ng/ml) | Number of Measurements | | | Standard Deviation (SD) | Average –2SD | Average | Average +2SD |
|---|---|---|---|---|---|---|---|
| | 1 | 2 | 3 | | | | |
| 0 | 0.007 | 0.007 | 0.005 | 0.001 | 0.004 | 0.006 | 0.009 |
| 1.5625 | 0.042 | 0.039 | 0.041 | 0.002 | 0.038 | 0.041 | 0.044 |
| 3.125 | 0.079 | 0.093 | 0.091 | 0.008 | 0.073 | 0.088 | 0.103 |
| 6.25 | 0.193 | 0.200 | 0.187 | 0.007 | 0.180 | 0.193 | 0.206 |
| 12.5 | 0.311 | 0.383 | 0.431 | 0.060 | 0.254 | 0.375 | 0.496 |
| 25 | 0.889 | 0.704 | 0.785 | 0.093 | 0.607 | 0.793 | 0.978 |
| 50 | 1.631 | 1.393 | 1.642 | 0.141 | 1.274 | 1.555 | 1.837 |
| 100 | 2.788 | 2.720 | 2.540 | 0.128 | 2.426 | 2.683 | 2.939 |

TABLE 2-3

Assay of 8M-urea-treated Human Annexin-V Antigen by Monoclonal Antibodies ELISA System
Combination of Monoclonal Antibodies for ELISA System: HRPO-labeled-HCA-155H Antibody and HCA-293HDR Solid Phase (Absorbance A492 nm − 690 nm)

| Concentration of 8M-urea-treated Human Annexin-V Antigen (ng/ml) | Number of Measurements | | | Standard Deviation (SD) | Average −2SD | Average | Average +2SD |
|---|---|---|---|---|---|---|---|
| | 1 | 2 | 3 | | | | |
| 0 | 0.004 | 0.009 | 0.007 | 0.003 | 0.002 | 0.007 | 0.012 |
| 1.5625 | 0.064 | 0.067 | 0.048 | 0.010 | 0.039 | 0.060 | 0.080 |
| 3.125 | 0.090 | 0.097 | 0.110 | 0.010 | 0.079 | 0.099 | 0.119 |
| 6.25 | 0.188 | 0.190 | 0.190 | 0.001 | 0.187 | 0.189 | 0.192 |
| 12.5 | 0.395 | 0.399 | 0.416 | 0.011 | 0.381 | 0.403 | 0.426 |
| 25 | 0.771 | 0.825 | 0.869 | 0.049 | 0.723 | 0.822 | 0.920 |
| 50 | 1.781 | 1.783 | 1.811 | 0.017 | 1.758 | 1.792 | 1.825 |
| 100 | 3.470 | 3.740 | 3.700 | 0.146 | 3.345 | 3.637 | 3.928 |

TABLE 2-4

Assay of 8M-urea-treated Human Annexin-V Antigen by Monoclonal Antibodies ELISA System
Combination of Monoclonal Antibodies for ELISA System: HRPO-labeled-HCA-155H Antibody and HCA-350HDR Solid Phase (Absorbance A492 nm − 690 nm)

| Concentration of 8M-urea-treated Human Annexin-V Antigen (ng/ml) | Number of Measurements | | | Standard Deviation (SD) | Average −2SD | Average | Average +2SD |
|---|---|---|---|---|---|---|---|
| | 1 | 2 | 3 | | | | |
| 0 | 0.006 | 0.006 | 0.006 | 0.000 | 0.006 | 0.006 | 0.006 |
| 1.5625 | 0.059 | 0.059 | 0.059 | 0.000 | 0.059 | 0.059 | 0.059 |
| 3.125 | 0.113 | 0.128 | 0.116 | 0.008 | 0.103 | 0.119 | 0.135 |
| 6.25 | 0.184 | 0.178 | 0.215 | 0.020 | 0.153 | 0.192 | 0.232 |
| 12.5 | 0.467 | 0.572 | 0.585 | 0.065 | 0.412 | 0.541 | 0.671 |
| 25 | 0.954 | 0.840 | 1.062 | 0.111 | 0.730 | 0.952 | 1.174 |
| 50 | 2.313 | 2.259 | 2.042 | 0.143 | 1.918 | 2.205 | 2.492 |
| 100 | 3.280 | 3.360 | 3.200 | 0.080 | 3.120 | 3.280 | 3.440 |

TABLE 2-5

Assay of 8M-urea-treated Human Annexin-V Antigen by Monoclonal Antibodies ELISA System
Combination of Monoclonal Antibodies for ELISA System: HRPO-labeled-HCA-660HD Antibody and HCA-290 Solid Phase (Absorbance A492 nm − 690 nm)

| Concentration of 8M-urea-treated Human Annexin-V Antigen (ng/ml) | Number of Measurements | | | Standard Deviation (SD) | Average −2SD | Average | Average +2SD |
|---|---|---|---|---|---|---|---|
| | 1 | 2 | 3 | | | | |
| 0 | 0.007 | 0.007 | 0.008 | 0.001 | 0.006 | 0.007 | 0.008 |
| 1.5625 | 0.052 | 0.052 | 0.053 | 0.001 | 0.051 | 0.052 | 0.053 |
| 3.125 | 0.121 | 0.116 | 0.107 | 0.007 | 0.100 | 0.115 | 0.129 |
| 6.25 | 0.257 | 0.243 | 0.211 | 0.024 | 0.190 | 0.237 | 0.284 |
| 12.5 | 0.497 | 0.427 | 0.494 | 0.040 | 0.394 | 0.473 | 0.552 |
| 25 | 0.950 | 0.977 | 0.842 | 0.071 | 0.780 | 0.923 | 1.066 |
| 50 | 2.142 | 2.124 | 2.038 | 0.056 | 1.990 | 2.101 | 2.212 |
| 100 | 3.980 | 3.590 | 3.810 | 0.196 | 3.402 | 3.793 | 4.184 |

TABLE 2-6

Assay of 8M-urea-treated Human Annexin-V Antigen by Monoclonal Antibodies ELISA System
Combination of Monoclonal Antibodies for ELISA System: HRPO-labeled-HCA-660HD Antibody and HCA-57HDR Solid Phase (Absorbance A492 nm − 690 nm)

| Concentration of 8M-urea-treated Human Annexin-V Antigen (ng/ml) | Number of Measurements | | | Standard Deviation (SD) | Average −2SD | Average | Average +2SD |
|---|---|---|---|---|---|---|---|
| | 1 | 2 | 3 | | | | |
| 0 | 0.007 | 0.008 | 0.008 | 0.001 | 0.007 | 0.008 | 0.009 |
| 1.5625 | 0.058 | 0.056 | 0.048 | 0.005 | 0.043 | 0.054 | 0.065 |
| 3.125 | 0.108 | 0.113 | 0.113 | 0.003 | 0.106 | 0.111 | 0.117 |
| 6.25 | 0.294 | 0.228 | 0.309 | 0.043 | 0.191 | 0.277 | 0.363 |
| 12.5 | 0.448 | 0.544 | 0.461 | 0.052 | 0.380 | 0.484 | 0.588 |
| 25 | 0.907 | 0.884 | 0.870 | 0.019 | 0.850 | 0.887 | 0.924 |
| 50 | 1.862 | 1.813 | 1.774 | 0.044 | 1.728 | 1.816 | 1.905 |
| 100 | 3.440 | 3.430 | 3.600 | 0.095 | 3.299 | 3.490 | 3.681 |

TABLE 2-7

Assay of 8M-urea-treated Human Annexin-V Antigen by Monoclonal Antibodies ELISA System
Combination of Monoclonal Antibodies for ELISA System: HRPO-labeled-HCA-660HD Antibody and HCA-293HDR Solid Phase (Absorbance A492 nm − 690 nm)

| Concentration of 8M-urea-treated Human Annexin-V Antigen (ng/ml) | Number of Measurements | | | Standard Deviation (SD) | Average −2SD | Average | Average +2SD |
|---|---|---|---|---|---|---|---|
| | 1 | 2 | 3 | | | | |
| 0 | 0.006 | 0.007 | 0.009 | 0.002 | 0.004 | 0.007 | 0.010 |
| 1.5625 | 0.076 | 0.074 | 0.086 | 0.006 | 0.066 | 0.079 | 0.092 |
| 3.125 | 0.157 | 0.117 | 0.114 | 0.024 | 0.081 | 0.129 | 0.177 |
| 6.25 | 0.233 | 0.223 | 0.247 | 0.012 | 0.210 | 0.234 | 0.258 |
| 12.5 | 0.516 | 0.492 | 0.490 | 0.014 | 0.470 | 0.499 | 0.528 |
| 25 | 1.030 | 0.927 | 1.056 | 0.068 | 0.868 | 1.004 | 1.141 |
| 50 | 2.042 | 2.535 | 2.167 | 0.256 | 1.735 | 2.248 | 2.761 |
| 100 | 4.010 | 4.060 | 4.230 | 0.115 | 3.869 | 4.100 | 4.331 |

TABLE 2-8

Assay of 8M-urea-treated Human Annexin-V Antigen by Monoclonal Antibodies ELISA System
Combination of Monoclonal Antibodies for ELISA System: HRPO-labeled-HCA-660HD Antibody and HCA-350HDR Solid Phase (Absorbance A492 nm − 690 nm)

| Concentration of 8M-urea-treated Human Annexin-V Antigen (ng/ml) | Number of Measurements | | | Standard Deviation (SD) | Average −2SD | Average | Average +2SD |
|---|---|---|---|---|---|---|---|
| | 1 | 2 | 3 | | | | |
| 0 | 0.007 | 0.008 | 0.009 | 0.001 | 0.006 | 0.008 | 0.0.010 |
| 1.5625 | 0.079 | 0.067 | 0.052 | 0.014 | 0.039 | 0.066 | 0.093 |
| 3.125 | 0.146 | 0.164 | 0.098 | 0.034 | 0.068 | 0.136 | 0.204 |
| 6.25 | 0.254 | 0.293 | 0.340 | 0.043 | 0.210 | 0.296 | 0.382 |
| 12.5 | 0.532 | 0.530 | 0.548 | 0.010 | 0.517 | 0.537 | 0.556 |
| 25 | 0.976 | 1.007 | 1.138 | 0.086 | 0.868 | 1.040 | 1.212 |
| 50 | 2.000 | 2.111 | 1.998 | 0.065 | 1.907 | 2.036 | 2.166 |
| 100 | 3.650 | 3.450 | 3.400 | 0.132 | 3.235 | 3.500 | 3.765 |

FIGS. 1 thorough 8 illustrate calibration curves for human annexin-V, in which the results of measurement as given in Tables 2-1 through 2-8 are plotted in diagrams with the absiccia being the concentration of human annexin-V antigen and the ordinate being the difference in the absorbance measured between at 492 nm and at 690 nm.

The calibration curves are excellent ones as the absorbance increases with increasing concentration of human annexin-V substantially linearly as high as a concentration of 100 ng/ml. The use of these calibration curves enables reliable assay of human annexin-V concentration in samples to be examined (plasma and serum). It is also possible to determine the concentration of human annexin-V with good reproducibility even as low as a concentration of 1 ng/ml, as can be seen FIG. 1. The calibration curves as shown by FIGS. 1 through 8 are of reliable use for the determination of the concentration of human annexin-V.

With the native human annexin-V without 8M-urea-treatment as the standard antigen, the absorbance detected was approx. 5% to 10% of that with 8M-urea-treated human annexin-V, demonstrating that the system has a low reactivity to the native human annexin-V antigen.

EXAMPLE 4

Assay of Human Annexin-V Using Anti-Human-Annexin-V Monoclonal Antibody HCA-627 and HRPO-Labeled-Anti-Dog-32KP-Annexin-V Polyclonal Antibody Assay of human annexin-V concentration was conducted by ELISA using anti-human-annexin-V monoclonal antibody HCA-627, which has been found to exhibit a high reactivity with native annexin-V without 8M-urea treatment, in combination with anti-dog-32KP-annexin-V polyclonal antibody.

Thus, 100 microliters of anti-human-annexin-V monoclonal antibody HCA-627, secreted from hybridoma cell line HCA-627 strain capable of producing an anti-human-annexin-V monoclonal antibody, was distributed in wells at a rate of 100 microliters per well, to prepare solid-phase well coupled with anti-human-annexin-V monoclonal antibody in the manner for preparing the solid-phase as described in Example 4 (5).

To the solid phase wells was added 10 mM sodium phosphate buffer (pH 7.0) containing 1% BSA, 0.15M NaCl and 5 mM EDTA at a rate 100 microliters per well.

Following the distribution of the reaction buffer, each well was added with a standard solution. As the standard solution in this Example were used standard solutions of 8M-urea treated human annexin-V antigen and standard solutions of native human annexin-V antigen. Thus, one set of the solid phase wells were added with the standard solution of 8M-urea-treated human annexin-V whereas the other set of the solid phase wells were added with the standard solutions of native annexin-V antigen. Following the distribution of the standard solutions, an antigen-antibody reaction was allowed to take place in each well with stirring for one hour. After the antigen-antibody reaction, each well was washed four times with the washing solution and then added with 100 microliters of the HRPO-labeled-anti-dog-annexin-V polyclonal Fab' antibody (100 mU per ml of the reaction buffer) followed by an antigen-antibody reaction for thirty minutes with stirring. Then, each well was washed eight times with the washing solution and added with 100 microliters of OPD substrate solution for the color production reaction at room temperature for thirty minutes.

With the lapse of the time for the color production, each well was added with the reaction-terminating solution (2N $H_2SO_4$ solution) to terminate the reaction, followed by absorbance measurements at the primary wavelength 492 nm and secondary wavelength 690 nm on an ELISA plate reader to assay the samples and the standard solutions for the concentration of human annexin-V.

The absorbance was obtained by subtracting an absorbance measured at the secondary wavelength 690 nm from that at the primary wavelength 492 nm. Thus, a calibration curve was prepared by plotting the absorbance data against the human annexin-V concentration with reference to the antigen protein standard solution. Based on such calibration curve, a sample can be calibrated for the concentration of the antigenic protein, human annexin-V.

In the Table 3 below, there are given absorbance data on the standard antigen of native annexin-V obtained by ELISA using anti-human annexin-V monoclonal antibody HCA-627 and the HRPO-labeled-anti-dog-32KP polyclonal antibody.

TABLE 3

Combination System in Assay of Native Annexin-V Antigen by ELISA Combination of HRPO-labeled anti-dog-32KP Polyclonal Antibody and Anti-human-annexin-V Monoclonal Antibody HCA-627 Solid Phase (Absorbance = A492 nm − 690 nm)

| Concentration of Native Annexin-V Antigen (ng/ml) | Number of Measurements 1 | 2 | Standard Deviation (SD) | Average −2SD | Average | Average +2SD |
|---|---|---|---|---|---|---|
| 0 | 0.018 | 0.019 | 0.001 | 0.017 | 0.019 | 0.020 |
| 1.5625 | 0.037 | 0.038 | 0.001 | 0.036 | 0.038 | 0.039 |
| 3.125 | 0.061 | 0.063 | 0.001 | 0.059 | 0.062 | 0.065 |
| 6.25 | 0.119 | 0.122 | 0.002 | 0.116 | 0.121 | 0.125 |
| 12.5 | 0.215 | 0.218 | 0.002 | 0.212 | 0.217 | 0.221 |
| 25 | 0.421 | 0.433 | 0.008 | 0.410 | 0.427 | 0.444 |
| 50 | 0.825 | 0.826 | 0.001 | 0.824 | 0.826 | 0.827 |
| 100 | 1.448 | 1.512 | 0.045 | 1.389 | 1.480 | 1.571 |

FIG. 9 illustrates a calibration curve prepared from the results of the assay as given in Table 3. Thus, the reliable calibration curve was obtained for the concentration of the native human annexin-V antigen in the ELISA system using the anti-human-annexin-V monoclonal antibody HCA-627 and the HRPO-labeled anti-dog-32KP polyclonal antibody.

EXAMPLE 5

Detection and Quantitative Analysis of Human Annexin-V in Samples from Patients with Myocardial Infarction, by ELISA Using Anti-Human-Annexin-V Monoclonal Antibody HCA-627 and HRPO-Labeled-Anti-Dog-32KP Polyclonal Fab'

The combination of anti-human-annexin-V monoclonal antibody HCA-627 and HRPO-labeled-anti-dog-32KP polyclonal Fab' prepared in the above-mentioned manner, which has been found to have an excellent sensitivity in assaying the native human annexin-V, was examined for its applicability to the assay of human annexin-V concentration in the clinical samples from patients with myocardial infarction.

Thus, the solid phase composed of anti-human-annexin-V monoclonal antibody was added, after discharging the solution, with 10 mM sodium phosphate (pH 7.0) containing 1% BSA, 0.15M NaCl and 5 mM EDTA at a rate of 100 microliters per well. Antigen standard solutions of native human annexin-V (1.5625 ng/ml, 3.125 ng/ml, 6.25 ng/ml, 12.5 ng/ml, 25 ng/ml, 50 ng/ml and 100 ng/ml) and human plasma samples are added each at a rate of 20 microliters per well, followed by stirring and an antigen-antibody reaction for one hour at room temperature. With the lapse of the time for the antigen-antibody reaction, each well was washed three times with the washing solution. Then, to the wells was added HRPO-labeled-anti-dog-32KP polyclonal Fab' antibody having been prepared to have an appropriate concentration (100 mU per ml of the reaction buffer) at a rate of 100 microliters per well, followed by an antigen-antibody reaction for thirty minutes at room temperature. With the lapse of the time for the antigen-antibody reaction, each well was washed eight times with the washing solution.

Following the washing, each well was added with 100 microliters of OPD substrate solution containing 0.1 m phosphate-citrate buffer, 2 mg/ml o-phenylenediamine and 4 mM $H_2O_2$, for color production reaction for thirty minutes at room temperature.

With the lapse of the time for the color production reaction, each well was added with 2N $H_2SO_4$ as reaction-terminating solution to terminate the color production reaction. The color produced in each well was assayed at the primary wavelength 492 nm and at the secondary wavelength 690 nm. The assay was conducted by measuring absorbance on an ELISA plate reader at the primary wavelength 492 nm and at the secondary wavelength 690 nm. The absorbance for a sample to be examined or for a standard solution was obtained by subtracting an absorbance measurement at the secondary wavelength 492 nm from that at the primary wavelength 690 nm, to determine the concentration of human cardiac-muscle annexin-V in the sample or the standard solution.

The measurements for the human plasma samples were obtained by reading the human annexin-V concentration in the respective samples with reference to the calibration curve which has been prepared based on the absorbance measurements of the standard solutions of varying human annexin-V concentration.

EXAMPLE 6

Application of the Enzyme-Antibody Method of the Invention to the Assay of Blood Samples (1) Diagnosis of Myocardial Infarction A 75-year-old man with a pain in the chest at 6:00 a.m. was hospitalized at 8:30 a.m. of the same day on suspicion of acute myocardial infarction because of abnormality on the electrocardiogram and the pain in the chest. At 9:00 a.m. of the day (i.e. three hours from the the attack) while CK (creatine phosphate enzyme) value indicated 108 U/L in the normal range, annexin-V was found to be an increased value of 90.4 ng/ml. With the lapse of three days from attack, annexin-V decreased down to 13.1 ng/ml. The abnormality on the electrocardiogram in this case indicated the finding of acute myocardial infarction and the assay of human annexin-V concentration in the plasma sample was found to be of use in a quick diagonsis of myocardial infarction.

It was later established that 70% of patients are diagnostic of myocardial infarction, in cases where the annexin-v concentrations in the plasma of the patients were determined to be 50 ng/ml or more as the annexin-V concentration in the blood of the patient with myocardial infarction is relatively high.

(2) Diagnosis of Angina Pectoris

An 58-year-old man, who complained of two times of pains in the chest attacked at 2:30 p.m. and 6:30 p.m. and continued over 10 to 15 minutes, was hospitalized at 7:30 of the same day on suspicion of angina pectoris because of abnormality in the electrocardiogram and the relatively short pain in the chest. While the CK value was a normal value of 83 U/L, the annexin-V concentration was an increased value of 29.9 ng/ml. The annexin-V value decreased down to 29.9 ng/ml at 12:00 and 15.1 ng/ml at 15:00 of the same day, demonstrating the restoration to normal. The case was assessed to be suspicions of angina pectoris because of the clinical symptom and the abnormality on the electrocardiodiagram was then diagnostic of angina pectoris, in which it was found that the concentration of human annexin-V in the plasma also increases in a case of angina pectoris.

The concentration of human annexin-V in the blood of a patient with angina pectoris is much higher than the normal value, although it is relatively low as compared with in the case of myocardial infarction. It was later established that 70% of the patients were diagnostic of angina pectoris, in cases where the human annexin-V concentrations in the plasma of the patients were determined to be 20 to 50 ng/ml.

(3) Annexin-V Concentration in the Blood from Normal Adults

Annexin-V concentration in the blood from normal male adults 24 to 76 years of age were determined to be 0.9 to 11.3 ng/ml, whereas those from normal female adults 24 to 76 years of age were 0.8 to 10.6 ng/ml, with the average being 6.2 ng/ml, the maximum 11.3 ng/ml and the minimum 0.8 ng/ml. However, there were observed no age-dependent variations.

EXAMPLE 7

Application of the Enzyme Antibody Method to Cardiac Muscle Tissue Specific Staining (1) The anti-human-annexin-V monoclonal antibodies obtained in Example 3 was applicable not only to an ELISA method but to staining specifically localized or distributed areas of human annexin-V in the cardiac muscle tissue by means of an indirect enzyme antibody method.

Furthermore, the use of the HRPO-labeled anti-human-annexin-V antibodies prepared in Example 4 makes it possible to make a short-time specific staining of the cardiac muscle tissue by means of a direct enzyme antibody method.

The following is given by taking the indirect enzyme antibody method as an example: paraffin-treated or frozen slices of the cardiac muscle tissue were fixed on a slide glass and allowed, following the paraffin-removal or blocking, to react with the anti-human annexin-V monoclonal antibodies having been prepared to have an appropriate concentration (IgG concentration: 500 to 1000 micrograms/ml) as the primary antibody at room temperature over an hour in a humid box. The resultant was then washed with phosplate-buffered saline (PBS) three times for five minutes each, followed by a reaction with HRPO-labeled anti-mouse-immunoglobulin antibodies as the secondary antibody for thirty minutes in a humid box. The resultant was washed three times for five minutes each, followed by addition of substrate solution of 4-aminoantipyrine type or diaminobenzidine for reaction over thirty minutes. On completing reaction, the slide-glass was washed with PBS and then sealed with a sealant such as glycerol through a covering glass, for a microscopic observation of the stained areas.

The results are given in FIGS. 10 and 11, in which the distribution of localized human annexin-V in the cardiac muscle tissue was stained with brown color and developed in black, demonstrating that the invention is applicable to a tissue-staining for cardiac muscle by means of an enzyme antibody method as well as to an ELISA.

EXAMPLE 8

Hybridoma Preparation (1) Mice

Inbred-strain BALB/c female mice 5 to 8 weeks of age were maintained on a diet of the standard pellets, feeding water ad libitum in an animal-breeding chamber ($23°+1°$ C., humidity 70%).

(2) Inmmunization

Dog-annexin-V extracted and purified from dog cardiac muscles (cf. Japanese Laid-open patent application No.72147/1995) and the human annexin-V purified from human cardiac muscles as described in Example 1 were each dissolved in 0.1M sodium phosphate buffer (pH 7.6) and dialyzed against the same buffer. Following the dialysis, the respective annexin-V antigens was prepared so as to give solutions of a concentration of 1 mg/ml, which were distributed into Eppen tubes at a rate of 50 microliters per tube, followed by freeze-drying at −400° C. to keep the purified native dog- and human-cardiac muscle-derived annexin-V antigens for immunization.

Dog annexin-V 0.2 ml (200 micrograms) as prepared in the above-mentioned manner was added with 0.3 ml of physiological saline to give a volume of 0.5 ml. The antigen solution thus prepared was mixed with 0.5 ml of Freund's complete adjuvant, followed by thorough emulsification. The dog annexin-V in emulsion as the antigen was administered into the abdominal cavities of four female mice of 5 week-of age in a dose of the purified dog annexin-V 40 micrograms per mouse for the intial immunization.

Dog annexin-V antigen 0.2 ml (200 micrograms) as prepared in the aforesaid manner was taken in a test tube, to which was added 0.3 ml of physiological saline to give a volume of 0.5 ml. The solution thus prepared was added with 0.5 ml of RIBI Adjuvant System (RAS) MPL+TDM Eumulsion R-700 (available from RIBI Immuno Chem. Research Inc., Hamilton, Mont., USA), in which 1 ml of plysiological saline was added per vial for making the solution. The resultant mixture was vigorously stirred in a vortex mixer for approx. three minutes for emulsification. With this dog annexin-V antigen in emulsion the mice were immunized as booster immunizations two weeks, four weeks and six weeks after the intial immunization in a dose of 50 maicrograms per mouse. A further booster immunization was carried out twenty-three weeks after the initial immunization in a dose of the dog annexin-V antigen 30 micrograms per mouse, with the antigen having been prepared in the same manner as mentioned above using RIBI Adjuvant System (RAS) MPL+TDM Emulsion, R-700. Following the booster immunization the blood was collected from the respective mice at intervals to prepare sera, which were assayed by the aforesaid absorption test for antibody titers against native dog cardiac muscle- and human-annexin-V to examine the production of specific antibodies. Based on the result of the assay for the antibody titer, mice were selected having a high titer. The selected mice were administered, twenty-six weeks after the initial immunization, with the native annexin-V (having been prepared by dissolving in 1 ml of physiological saline to give a concentration of 50 micrograms/ml) intravenovsly through the mice tails as a booster. At this point the mouse sera were again assayed for the antibody titer to select mice having a higher titer. The selected mice were administered, one week after the preceding booster immunization, with 1 ml of the native human annexin-V (having been prepared with physiological saline to give a concentration of 100 micrograms/ml) slowly and intravenously through the tails of the mice for final immunization.

(3) Preparation of Spleen Cells

Three days after the final immunization, the spleen were excised from the BALB/c mice in the same manner as described in Example 1. The excised spleen cells were suspended in EMEM culture medium (available from Nissui Co.) to prepare a suspension of spleen cells. The spleen cells were washed four times with EMEM culture medium and determined for the number of cells. The resultant spleen cells are $4.7 \times 10^8$.

(4) Preparation of Parent Strain

Cell fusion was conducted using P3-X63-Ag8.653 culture cells (hereinafter referred to as X63 cells) as parent cell strain, which are 2-amino-6-oxy-8-azapurine (8-Azaguanine) -resistant and derived from BALB/c mouse myeloma.

X63 cells in the logarithmic growth phase were employed to subculture in RPMI-1640 medium (in a concentration of 20 micrograms/ml and with 8-azaguanine) (available from GIBCO Co.) containing 10% of immobilized fatal calf serum (hereinafter referred to as FCS). Further cultivation was carried out, from three days in advance to the cell fusion, in RPMI-1640 culture medium containing 10% FCS but not containing 8-azaguanine to maintain the growth ability in the logarithmic phase. The X 63 cells were washed three times with RPMI-1640 medium and determined for the number of cells. The number of living X63 cells was $1.5 \times 10^8$.

(5) Cell Fusion

Polyethylene glycol-400 available from Sigma Co. was dissolved in RPMI-1640 culture medium to give a concentration of 50% (W/V), followed by heating at 37° C. for use.

The spleen cells and X63 cells were mixed together in a ratio of the spleen cells: the X63 cells=10:1. The mixture was centrifuged at 1500 rpm for five minutes, the supernatant was removed and the pelletized cells were thoroughly disintegrated for use in cell fusion. The cell fusion was conducted, using polyethylene glycol prepared in the aforesaid manner and kept at 37° C., in accordance with the method described in "Köhler and Milstein: Nature, Vol.256, pages 495–497 (1975)" and "European Journal of Immunology, Vol.6, pages 511–519 (1976)".

The cell line following the cell fusion were suspended in HAT selection medium containing RPMI-1640 added with FCS of a 10% concentration, $1 \times 10^{-4}$ hypoxanthine, $4 \times 10^{-7}$ aminopterin and $1.6 \times 10^{-5}$M thymidine, to give a spleen-cell concentration of $2.0 \times 10^6$ per ml. The cell suspension was distributed in a 96-well microtitreplate at a rate of 50 microliters per well, and incubated in an incubator kept at a 37° C. temperature and a 95% humidity under a 8% $CO_2$ atomsphere. One drop of the HAT medium was added to each well on the first day and the second day from the start of the incubation, followed by the addition of two drops of the same medium seven and nine days after start, for further incubation. Then, incubation was carried out in a HAT-free culture medium. Appox. ten days to two weeks after the start of incubation, screening was made, as the first screening, for clones producing anti-annexin-V monoclonal antibodies having a common reactivity to native human annexin-V and native dog annexin-V, in which the screening was done by an annexin-V absorption test using the native human annexin-V and dog annexin-V antigens.

The selected clones were then subjected to the second screening by means of a capture method for monoclonal antibodies, through which were selected hybridoma cell line clones producing monoclonal antibodies suitable for use in a sandwich ELISA system for a sensitive assay of annexin-V in combination with monoclonal antibodies HCA-627. The monoclonal antibodies HCA-627 are produced by hybridoma cell line HCA-627 strain which has been deposited under the number BP-5284 at the National Institute of Bioscience and Human-Technology, the Agency of Industrial Aeience and Technology of Japan.

(6) Screening (i) First Screening

As cell clones appeared ten days after the start of incubation, the absorption test with native dog- and human-annexin-V as the antigens was carried out by ELISA for the supernatants of the hybridoma cell line cultures.

It was found by the present inventors that an ELISA system employing a combination the monoclonal antibodies HCA-627 bound to the cells as the solid phase and the HRPO-labeled anti-dog-32KP polyclonal antibodies can be applied to the assay of native human annexin-V and dog annexin-V antigens. The system was thus utilized to screen monoclonal antibodies which will efficiently react with the native annexin-V.

Thus, the first set was constituted of the supernatant of hybridoma cell line clone culture obtained by the subject cell fusion and the native human annexin-V antigen solution (100 ng/ml) with each being distributed in U-bottomed wells of a microtitreplate at a rate of 50 microliters per well, while the second set was constituted of the supernatant of the same hybridoma cell line clone culture and the native dog annexin-V antigen solution (100 ng/ml) with each being distributed in a plurality of U-bottomed wells of another microtitreplate at a rate of 50 microliters per well.

Each set was added with 50 microliters of 20% suspension of Sepharose 4B combined with anti-mouse-immunoglobulin antibody and allowed to stand for 10 minutes following stirring for the one hour. With each set, when it was observed that the anti-mouse-immunoglobulin antibody-combined sepharose 4B completely sedimented on the well-bottoms, the respective supernatants 50 microtilers were assayed for human annexin-V or dog annexin-V content remaining therein by means of the aforesaid annexin-V ELISA method.

(ii) Selection of Monoclonal Antibodies by the First Screening

In this assay, if any anti-cardiac-muscle-annexin-V monoclonal antibodies against native dog- and human-annexin-V remain in the culture supernatant of a hybridoma cell line, a reaction will occur between the native dog- or human-annexin-V and the anti-human-annexin-V monoclonal antibodies, followed by a reaction with anti-mouse-immunoglobulin monoclonal antibody-combined Sepharose 4B, resulting in the formation of antigen-antibody complexes which are to sediment. This will lead to a decrease in the annexin-V content remaining in the supernatant and it is therefore possible to identify the occurrence of any anti-annexin-V monoclonal antibodies.

(iii) Second Screening

If there were successfully selected anti-annexin-V monoclonal antibodies having a reactivity with native human- and dog-annexin-V antigens, screening was then made, through the following capture ELISA, for hybridoma cell line clones producing any monoclonal antibodies suitable for establishing a sandwich ELISA system for sensitive assay of annexin-V, in combination with the monoclonal antibodies HCA-627 produced by hybridoma cell line HCA-627 strain which has been deposited as an International Deposit under the number FERM BP-5284.

(iv) Capture ELISA Method

A solution was prepared of the IgG fraction of polyclonal antibody having a specificity to the Fc portion of goat-derived anti-mouse immunoglobulin (available from Nordic Co.), with 0.1M sodium phosphate solution (pH 7.5) containing 0.1% sodium azide to give a concentration of 50 microliters/ml. The solution was distributed in a 96-well titerplate (available from Nunk Co.) at a rate of 50 microliters per well for adsorption at 4° C. overnight.

The resultant was then washed three times with washing phosphate buffer (hereinafter referred to washing solution) containing 0.05% Tween-20, followed by blocking with PBS containing 1% BSA to prepare anti-mouse-immunoglobulin G-Fc polyclonal antibody-bound wells as the solid phase.

(v) Based on the results of the absorption test with native human- and dog-annexin-V, the culture supernatants of hybridoma cell lines producing monoclonal antibodies with a high reactivity with the native human- and dog annexin-V was added into the wells bound with the anti-mouse-immunoglobulin G-Fc polyclonal antibody as the solid phase at a rate 50 microliters per well, following the removal of the blocking solution from each well. Upon the completion of reaction for one hour at room temperature, each well was washed three times with the washing solution. With a phosphate buffer of pH 7.0 containing 1% BSA and 5 mM EDTA (hereinafter reaction buffer solution), a solution of native human annexin-V was prepared to give a concentration of 100 ng/ml. To each well was added 50 microliters of the solution of native human annexin-V, for a further reaction over one hour, followed by washing three times with the washing solution. HRPO-labeled HCA-627-Fab' antibody were conditioned with the reaction buffer solution to have an appropriate concentration, and then added to the respective wells for reaction over thirty minutes. The dilution of the HRPO-labeled antibodies was done in such manner that the mouse immunoglobulin was 10 micrograms/ml, in order to block the adsorption of the HRPO-labeled antibodies onto the well bound with the anti-mouse-immunoglobulin G-Fc polyclonal antibodies as the solid phate. On completing the reaction, each well was washed three times with the washing solution, followed by reaction with OPD substrate solution (containing 0.1M phosphate-citrate buffer added with 2 mg/ml o-phenylenediamine and 4 mM $H_2O_2$) for five minutes at room temperature. The reaction was terminated with 2N $H_2SO_4$, to determine absorbance at the primary wavelength 492 nm and at the secondary wavelength 690 nm on an ELISA plate reader. Measurements at the primary wavelength 492 nm are attributed to the substrate chromogen produced by the bound labeled-antibody, whereas the measurements at the secondary wavelength reflect flaws or stains on the microtiter-plate.

By subtracting an absorbance measurement at the secondary wavelength from an absorbance measurement at the primary wavelength, it is possible to determine the true absorbance in response to the amount of chromogen changed due to the enzyme on the labeled-antibodies which have been bound to antigen in proportion to the amount of the antigen bound to the solid-phase.

This second screening enables obtainment of an annexin-V monoclonal antibody having reactivities with the native human- and dog-annexin-V antigens and being capable of recognizing an antigen determinant site different from another site on the indentical annexin-V molecule to be recognized by anti-annexin-V monoclonal antibody HCA-627, thereby providing an optimal combination with the anti-annexin-V monoclonal antibody HCA-627 for a sandwich ELISA system. Thus, a hybridoma cell line can be obtained which produces the monoclonal antibody to provide the optimal combination with the anti-human-annexin-V monoclonal antibody HCA-627 for the sandwich ELISA system.

(7) Studies on Reactivities with the Solid-Phases, Sensitized with Annexin-V Antigens Derived from Various Animals Studies were made on animal-dependent reactivities of the various anti-annexin-V monoclonal antibodies identified by the aforesaid screening, by allowing them to react with microtiterplate solid phases composed of annexin-V antigens extracted and purified from various animals.

(8) Preparation of Microtiterplates with Solid Phase-Coupled Native Annexin-V Antigens Native annexin-V antigens extracted and purified from the human heart, the dog heart, the rat heart and the bovine lung were each adjusted with 0.1M phosphate buffer at pH 7.5 to give an antigen solution of 1 microgram/ml. Each antigen solution was distributed in a 96-well microtiterplate (available from Nunk Co.) at a rate of 50 microliters per well, followed by adsorption at 4° C. overnight, washing three times with the washing solution and then blocking at 4° C. overnight with the blocking solution. Thus, the solid phase wells sensitized with various annexin-V antigens were prepared for use.

Studies were made of the anti-annexin-V monoclonal antibodies produced by the hybridoma cell lines obtained by the above described screening, with respect to their reactivities with the various annexin-V antigens bound to the plates as solid phase. Thus, reaction was performed, at room temperature for one hour, of the respective culture supernatants of hybridoma cell line clones producing the various anti-annexin-V monoclonal antibodies (the original solutions) or their purified IgG fractions (prepared to give a final concentration of 1 microgram/ml) with the respective solid phase wells sensitized with the native annexin-V antigens derived from the various animals, followed by washing three times with the washing solution. A further reaction was carried out with HRPO-labeled anti-mouse-immunoglobulin antibodies (derived from goats) at room temperature for thirty minutes, followed by washing four times with washing solution and reaction with OPD substrate solution (containing 0.1M phosphate-citrate 4 mM $H_2O_2$) at room temperature for thirty minutes. Then the reaction was terminated with 2N $H_2SO_4$ solution for absorbance assay at the primary wavelength 492 nm and the secondary wavelength 690 nm on an ELISA plate reader. Measurements at the primary wavelength 492 nm are attributed to the substrate chromogen produced by the bound labeled-antibody, whereas the measurements at the secondary wavelength reflects the detection of flaws or stains on the microtiterplate.

By subtracting an absorbance measurement at the secondary wavelength from an absorbance measurement at the primary wavelength, it is possible to determine the true absorbance in response to the amount of chromogen changed due to the enzyme on the labeled-antibodies which have been bound to antigen in proportion to the amount of the antigen bound to the solid-phase.

(9) Cloning

Based on the absorption test using the native human- and dog-annexin-V and through the above described capture ELISA system, the selection was made of hybridoma cell line clones which produce anti-annexin-V monoclonal antibodies to provide a prospective sensitive sandwich ELISA system for assaying native annexin-V in combination with the anti-annexin-V monoclonal antibody produced by hybridoma cell line HCA-627 strain (deposited under the number FERM PB-5284 at the National Institute of Bioscience and Human-Technology,the Agency of Industrial Science and Technology, Japan). The hybridoma cell line clones were subjected to a cloning operation by means of limiting dilution to obtain a single clone. In performing the cloning, thymus cells prepared from BALB/c mice and suspended in HAT medium was added as feeder cells at $1\times10^6$ per well.

(10) Identification of Mouse Immunoglobulin Subclass

Identification of mouse immunoglobulin subclass was made with respect to the monoclonal antibodies produced by the hybridoma cell lines which have been prepared as having a single clone by means of the above-mentioned cloning. The culture supernatants of the respective hybridoma cell lines were assayed for the mouse immunoglobulin subclass identification using MONOAb typing kit (available from Zymed Co.).

(11) Establishment of Hybridoma Cell Lines Producing Anti-Annexin-V Monoclonal Antibodies As a result of the first screening for the subject cell fusion, 200 strains were obtained which were positive in the absorption test using the native human- and dog-annexin-V antigen. In addition, the second screening through the above described capture ELISA were selected 8 clones, which can establish the sandwich ELISA system in combination with anti-annexin-V monoclonal antibody produced by hybridoma cell line HCA-627 strain deposited as an International Deposit under the number FERM BP-5284. Cloning through the limiting solution was conducted with regard to said eight elones to establish the respective hybridoma cell clones. Table 4 below gives reaction specificities of the anti-annexin-V monoclonal antibodies obtained by the subject cell fusion, No.2.

In table 4 there are given, for comparison, the reactivities of clones HCA-627, HCA-155H, HCA-507HD and HCA-293HDR obtained in the previous cell fusion of Example 1.

Different from the clones established in Example 1 (HCA-115H, HCA-507HD and HCA-293HRD), all the anti-annexin-V monoclonal antibodies produced by hybridoma cell line clones established in the subject Example demonstrate to have a high reactivity with the native human- and dog-annexin-V (cf. the absorption tests in Table 4).

It is also shown from the screening by the capture ELISA system that the clones are able to provide an efficient and sensitive sandwich ELISA system in combination with the anti-annexin-V monoclonal antibody produced by hybridoma cell line clone HCA-627 strain (deposited as an International Deposit under the number FERM BP-5284) (cf. the Capture Method in Table 4).

In addition, from the studies of the reaction system in which annexin-V antigens from humans and the various animals are bound as solid phase it was found that the hybridoma cell line clones established in the subject Example have a reactivity as monoclonal antibody totally different from some of the clones established in Example 1, HCA-115H, HCA-507HD and HCA-293HDR, as they do not exhibit any reactivity with the antigens of bound annexin-V as the solid phase derived from such animals (cf. Table 4), although they exhibit a strong reactivity with native annexin-V in the absorption test, i.e. with the antigens in liquid phase.

As can be seen from the above, the eight strains as screened by the capture ELISA system, anti-annexin-V monoclonal antibody-producing clones, are all capable of providing a sandwich ELISA system in combination with the monoclonal antibody clone HCA-627 (Table 4) and recognizing an epitope totally different from one to be recognized by the clone HCA-627.

As given in Table 4, the immunoglobulin subtypes of the anti-annexin-V monoclonal antibodies produced by the eight strains of hybridoma cell line clones established in the subject Example are all IgG type, with respect to the H chain. Regarding the L chain all the clones have k-chain (cf. Table4).

TABLE 4

Reaction Specificities of Anti-annexin-V Monoclonal Antinodies

| Cell fusion No. 2 Anti-human- and Anti-dog-annexin-V Mab clone No. | Mouse Immunoglobluin Isotype | | Absorption Test with Native Human Annexin-V Antigen Mab Reaction Concentration | | Absorption Test with Native Dog Annexin-V Antigen Mab Reaction Concentration | | Mab Screening by Mab Capture ELISA using Anti-mouse-IgG-Fc Solid-phase in Combination with HRPO-labeled HCA-627 Antibody Human-annexin-V Concentration | |
|---|---|---|---|---|---|---|---|---|
| | | | 10 µg/ml Absorption Rate (%) | 1 µg/ml Absorption Rate (%) | 10 µg/ml Absorption Rate (%) | 1 µg/ml Absorption Rate (%) | 0 ng/ml | 100 ng/ml |
| HCA-627 | IgG1 | k | 98 | 81 | 98 | 81 | 0.011 | 0.032 |
| HCA-155H | IgG2a | k | 4 | 1 | 4 | 2 | — | — |
| HCA-507HD | IgG2a | k | 7 | 3 | 7 | 5 | — | — |
| HCA-293HDR | IgG2a | k | 2 | 7 | 4 | 2 | — | — |
| HDA-202 | IgG1 | k | 98 | 80 | 97 | 78 | 0.011 | 2.830 |
| HDA-676 | IgG1 | k | 100 | 98 | 100 | 99 | 0.013 | 6.270 |
| HDA-907 | IgG1 | k | 98 | 75 | 99 | 79 | 0.010 | 3.220 |
| HDA-1018 | IgG1 | k | 98 | 82 | 99 | 91 | 0.011 | 4.430 |
| HDA-1606 | IgG1 | k | 97 | 68 | 98 | 77 | 0.005 | 2.615 |
| HDA-1884 | IgG1 | k | 96 | 64 | 98 | 68 | 0.014 | 2.643 |
| HDA-1937 | IgG1 | k | 99 | 98 | 100 | 99 | 0.012 | 9.080 |
| HDA-2003 | IgG1 | k | 99 | 98 | 100 | 99 | 0.013 | 7.170 |

Reactivities with Solid-phase plates Sensitized with Annexin-V Antigens from Various Animals

| Reactivity with Solid-phase-plate Sensitized with Native Annexin-V Antigen from Human Heart 50 µl/well Sensitization with 1 µg/ml Antigen Reaction of 1 µg/ml Mab A492 nm–A690 nm | Reactivity with Solid-phase-plate Sensitized with Native Annexin-V Antigen from Dog Heart 50 µl/well Sensitization with 1 µg/ml Antigen Reaction of 1 µg/ml Mab A492 nm–A690 nm | Reactivity with Solid-phase-plate Sensitized with Native Annexin-V Antigen from Rat Heart 50 µl/well Sensitization with 1 µg/ml Antigen Reaction of 1 µg/ml Mab A492 nm–A690 nm | Reactivity with Solid-phase-plate Sensitized with Native Annexin-V Antigen from Bovine Lung 50 µl/well Sensitization with 1 µg/ml Antigen Reaction of 1 µg/ml Mab A492 nm–A690 nm | Remarks |
|---|---|---|---|---|
| 0.020 | 0.001 | 0.002 | 0.013 | Established in Cell fusion No. 1 |
| 1.986 | 0.001 | 0.006 | 3.540 | See Table 1 Cell fusion No. 1 |
| 2.122 | 0.001 | 0.008 | 3.340 | See Table 1 on Cell fusion No. 1 |
| 1.950 | 1.688 | 0.735 | 3.680 | See Table 1 on Cell fusion No. 1 |
| 0.007 | 0.000 | 0.000 | 0.000 | |
| 0.008 | 0.000 | 0.000 | 0.010 | |
| 0.012 | 0.005 | 0.000 | 0.001 | |
| 0.006 | 0.000 | 0.001 | 0.005 | |
| 0.010 | 0.000 | 0.001 | 0.002 | |
| 0.008 | 0.003 | 0.083 | 0.001 | |
| 0.007 | 0.004 | 0.003 | 0.014 | |
| 0.009 | 0.000 | 0.000 | 0.010 | |

Mab: Monoclonal Antibody

EXAMPLE 9

Production of Monoclonal Antibodies (1) Harvesting of Ascitic Fluids

In order to obtain anti-annexin-V monoclonal antibodies of a higher concentration the various hybridoma cell lines are grown and the resulting respective clones were innoculated, following washing three times with EMEM culture solution, into the ascitic cavities of BALB/c mice which have been administered with 2, 6, 10, 14-tetramethyl pentadecane (pristane) in advance into their ascitic cavities. The ascitic fluids were harvested seven to fourteen days after the innoculation of the hybridoma cell lines into the ascitic casities. The ascitic fluids thus obtained were applied to a centrifuge to remove the cellular and residual fractions. The supernatant fractions were pooled for keeping at 4° C. with the addition of sodium azide as antiseptic.

(2) Purification of Monoclonal Antibodies from Ascitic Fluids

The IgG fractions of the monoclonal antibodies were obtained by applying the ascitic fluids obtained from the hybridoma cell lines to affinitychromatograpy using ConSep LC100 device and a protein-A column (available from Perceptive Co.). The purified IgG fractions of the respective clones were determined for purity by HPLC using a TSK gel G3000SW column (available from Tosoh Co.) and SDS-PAGE using PharstSystem (available from Pharmacia Co.). The result was that all the monoclonal antibodies from the hybridoma cell lines have a purity of 98% or more.

EXAMPLE 10

Studies on ELISA System for Assay of Human Annexin-V (1) Preparation of HRPO-Labeled Anti-Annexin-V Monoclonal Antibodies Studies were made on the applicability of the monoclonal antibodies as estatleshed in the above to an ELISA system for assay of native human annexin-V.

Thus, as representatives there were selected anti-annexin-V monoclonal antibodies HDA-676, HDA-907, HDA-1606 and HDA-1937, which had been produced by the anti-annexin-V monoclonal antibody-producing hybridoma cell line clones. The selected monoclonal antibodies were applied to affinity purification using a ConSepLC 100 device and a protein-A column (available from Perceptive Co.) to purify the IgG fractions.

(2) Preparation of Horseradish Peroxidase (HRPO) Labeled Monoclonal Antibodies (A) Preparation of Anti-Human-Annexin-V Monoclonal Antibodies F(ab')$_2$ For labeling the IgG fractions of the anti-annexin-X monoclonal antibodies, the purified IgG fractions of the respective anti-annexin-V monoclonal antibodies HDA-676, HDA-907 (deposited as an International under the number FERM BP-5286 at the National Institute of Bioscience and Human-Technology, the Agency of Industrial Science and Technology of Japan), HDA-1606 and HDA-1937 were each concentrated by a Centricon 10 centifugal concentrator (available from Amicon Co.) to give a concentration of 1 ml from 10 mg. The resultant was then dialyzed against 0.1M sodium acetate buffer (pH 3.7) containing 0.2M NaCl as solvent. Each dialyzed IgG solution was added with pepsin in an amount of 4% of IgG for reaction at 37° C. over 2 to 4 hours. On completing the reaction, the resultant was applied to molecular-sieve chromatography using a Sephadex G-150 column (available from Pharmacia Co.) equilibrated with 0.1M borate buffer (pH 8.0) to obtain the F(ab')$_2$ fragment. With every clone, 10 mg of the IgG fraction provided approx. 5 mg of F(ab')$_2$ fraction with a high yield. There was almost no difference in yield among the clones.

(B) Preparation of Anti-Annexin-V Monoclonal Antibodies Fab'-SH

Each of the anti-annexin-V monoclonal antibodies F(ab')$_2$ from HDA-676, HDA-907, HDA-1606 and HDA-1937, as prepared in the above method (A), was subjected centrifugal concentration by a Centricon 10 centrifugal concentrator to give 1 ml of each anti-annexin-V monoclonal antibody F(ab')$_2$ fraction.

To each concentrated fraction 1 ml was added with 0.1 ml of 100 mM 2-mercaptoethylamine hydrochloride solution (available from Kishida Chemicals Co.) for reaction at 370° C. for 90 minutes. On completing the reaction, the resultant was purified using a Sephadex G-25 column for equilibrium gel filtration measuring 1.6 cm in diameter and 20 cm in length (available from Pharmacia Co.) and equilibrated with 0.1M sodium phosphate buffer (pH 6.0) containing 1 mM EDTA, to fractionate the Fab'-SH fraction. Following the fractionation, the resultant purified fraction was pooled for centifugal concentration with a Centricon 10 centifugal concentrator to give a volume of 1 ml. Thus, the concentrated anti-annexin-V monoclonal antibodies Fab'-SH fractions were obtained from the respective clones: HDA-676, HDA-907, HDA-1606 and HDA-1937.

(C) Preparation of HRPO Maleimide 20 mg (as protein content) of HRPO (available from Boehlinger Co.) was dissolved in 1 ml of 0.1M sodium phosphate buffer (pH 6.0). The resulting solution was added with 100 microliters of solution of N-hydroxysuccinimi ester (available from Zeeben Chemicals Co.) dissolved in dimethyl formanide (DMF ) ( available from Kishida Chemicals Co.) to give a final concentration of 25 mg/l, followed by reaction at 30° C. for 60 minutes to prepare maleimide ester of HRPO. On completing the reaction, the solution was centrifuged for five minutes at 3000 rpm. The supernatant was applied to a Sephadex G-25 column for equilibrated gel filtration (available from Pharmacia Co.) measuring 1.6 cm in diameter and 20 cm in length, which has been equilibrated with 0.1M sodium phosphate buffer (pH 6.0), in order to purify HRPO maleimide. The purified fraction of HRPO maleimide was then subjected to centrifugal concentration by a Centricon 10 centrifugal concentrator to prepare the concentrated fraction of HRPO maleimide.

(D) Preparation of HRPO-Labeled Anti-Annexin-V Monoclonal Antibodies Fab'

The concentrated Fab'-SH fraction of the anti-annexin-V monoclonal antibody was mixed with the concentrated fraction of HRPO maleimide at a molar ratio of 1:1, for reaction at 4° C. for 15 to 24 hours. On completing the reaction, 2-mercaptoethylamine was added to give a final concentration of 2 mM in the reaction solution, followed by reaction at 37° C. for 20 minutes in order to block unaltered HRPO maleimide. The resultant was then subjected to molecular-sieve gelchromatography using a Ultragel ACA44 column (available from Pharmacia Co.) equilibrated with 20 mM sodium phosphate-sodium citrate buffer (pH 5.6) containing 0.15M NaCl and 2.5M EDTA and measuring 1.6 cm in diameter and 65 cm in length, for removing unaltered Fab'-SH of the auti-annexin-V monoclonal autibodies and unaltered HRPO maleimide and purifying the respective, HRPO-labeled anti-annexin-V monoclonal antibodies Fab' (hereinafter referred to as HRPO-labeled anti-annexin-V monoclonal antibodies).

(E) Activity Determination of HRPO-Labeled Antibodies

In determining HRPO enzyme activity of the HRPO-labeled antibodies, 2.98 ml of 0.1M sodium phosphate buffer (pH 7.0) containing 0.2% phenol, 0.5 mM hydrogen peroxide and 0.15 mg/ml 4-amino antipyrine was added with 20-microliters of the HRPO-labeled antibody to give a total volume of 3.0 ml, followed by reaction at 37° C. for five minutes, and measurement of absorbance at 500 nm by means of the Rate assay. HRPO activity was determined by measuring the difference in absorbance ($\Delta$Abs) for one minute.

(6) Preparation of Anti-Annexin-V Monoclonal Antibody Solid Phase Coupled Wells

In order to obtain monoclonal antibody for use as solid phase in an ELISA system for assay of human annexin-V, monoclonal antibody HDA-627, produced by hybridoma cell line HCA-627 strain which has been deposited under the number FERM BP-5284 at the International Depositary Authority for the deposit of microorganism, was applied to affinity purification using ConSepLC-100 device and a protein A column (available from Perceptive Co.) to purify the IgG fraction from the ascitic fluid.

The IgG fraction of anti-annexin-V monoclonal antibody HCA627 was adjusted to have a concentration of 30 micrograms/ml with 0.1M sodium phosphate buffer (pH 7.5) containing 0.1% sodium azide, and distributed in a microtitreplate for ELISA (available from Nunk Co.) at a rate of 100 microliters per well, for sensitization at 4° C. overnight. Then each well of the microtitreplate was washed three times with phosphate-buffered saline (PBS) containing 0.05% Tween 20 surfactant, and then added with 300 microliters of PBS containing 1% BSA (as the blocking solution), followed by a further blocking operation at 4° C. overnight, to prepare antibody-plates sensitired with anti-human-annexin-V monoclonal autibodies (hereinafter referred to as auti-human-annexin-V monoclonal antibody plates).

(7) Studies on ELISA Assay System Using Anti-Annexin-V Monoclonal Antibodies

The anti-annexin-V monoclonal antibody plates as prepared above were added, following discarding the blocking solution, with phosphate buffer of pH 7.0 (reaction buffer) containing 1% BSA and 5 mM EDTA at a rate of 100 microliters per well. Standard antigen solutions were prepared so as to give native annexin-V standard antigen concentrations of 1.563 ng/ml, 3.125 ng/ml 6.25 ng/ml, 12.5 ng/ml, 25 ng/ml, 50 ng/ml and 100 ng/ml. The respective standard antigen solutions were added to the wells at a rate of 20 microliters per well, followed by stirring and reaction at room temperature for one hour. On completing the reaction, each well was washed three times with the washing solution. Then, to the wells were added the HRPO-labeled anti-annexin-V monoclonal antibodies Fab' (clones: HDA-676, HDA-907, HDA-1606 and HDA-1937) at a rate of 100 microliters per well, for reaction at room temperature for thirty minutes. Following the reaction, each well was washed six times with the washing solution and then added with 100 microliters of OPD substrate solution containing 0.1M phosphate-citrate buffer added with 2 mg/ml o-phenylenediamine and 4 mM $H_2O_2$, for reaction for thirty minutes. The reaction was terminated by adding 2N $H_2SO_4$ solution at a rate of 100 microliters per well. Absorbance was determined on an ELISA plate reader at the primary wavelength 492 nm and at the secondary wavelength 690 nm.

The absorbance herein intended is obtained by subtracting an absorbance measurement at the secondary wanelength 690 nm from that at the primary wanelength 492 nm.

The results of absorbance measurements with respect to the representative native annexin-V standard antigen solutions were given in Table 5.

TABLE 5

Combination of Monoclonal Antibodies in Assay of Native Human Annexin-V Antigen by Monoclonal Antibodies ELISA system: Combination of HRPO-labeled HDA-907 Antibody and HCA-627 Solid-phase (Absorbance = A492 nm–690 nm)

| Concentration of Native Human Annexin-V Antigen (ng/ml) | Number of Measurements | | | | Average | Standard Deviation (SD) | Standard Error CV (%) |
|---|---|---|---|---|---|---|---|
| | 1 | 2 | 3 | 4 | | | |
| 0 | 0.006 | 0.007 | 0.007 | 0.006 | 0.007 | 0.0006 | 8.88 |
| 1.5625 | 0.080 | 0.080 | 0.077 | 0.077 | 0.079 | 0.0017 | 2.21 |
| 3.125 | 0.164 | 0.165 | 0.167 | 0.167 | 0.166 | 0.0015 | 0.90 |
| 6.25 | 0.321 | 0.320 | 0.314 | 0.324 | 0.320 | 0.0042 | 1.31 |

TABLE 5-continued

Combination of Monoclonal Antibodies in Assay of Native Human Annexin-V Antigen by Monoclonal Antibodies ELISA system: Combination of HRPO-labeled HDA-907 Antibody and HCA-627 Solid-phase (Absorbance = A492 nm–690 nm)

| Concentration of Native Human Annexin-V Antigen (ng/ml) | Number of Measurements | | | | Average | Standard Deviation (SD) | Standard Error CV (%) |
|---|---|---|---|---|---|---|---|
| | 1 | 2 | 3 | 4 | | | |
| 12.5 | 0.614 | 0.632 | 0.615 | 0.631 | 0.623 | 0.0098 | 1.58 |
| 25 | 1.126 | 1.152 | 1.113 | 1.124 | 1.129 | 0.0165 | 1.46 |
| 50 | 2.047 | 2.061 | 2.096 | 2.106 | 2.078 | 0.0285 | 1.35 |
| 100 | 4.120 | 3.940 | 4.180 | 3.870 | 4.028 | 0.1464 | 3.63 |

FIG. 12 illustrates a calibration curve for human annexin-V obtained by plotting the measurements on the human annexin-V antigen solutions with standard antigen solution absorbance as ordinate and human annexin-V antigen concentration as abscissa.

The calibration curve as shown in FIG. 12 is excellent one, as it demonstrates that the absorbance rises with increasing concentration of human annexin-V, substantially linearly from a low concentration up to as high as 100 ng/ml.

The calibration curve also indicates that the subject example enjoys a wider dynamic range and hence provides a more sensitive system, as compared with the calibration curve for native human annexin-V antigen in which there was employed the combination of the monocloval antibody as solid phase produced by hybridoma cell line clone HCA-627 strain deposited under the number FERM BP-5284 as an International Deposit with HRPO-labeled anti-32KP polyclonal Fab' antibody.

It should be noted, however, that the combination of the anti-annexin-V monocloval antibody HCA-627 as solid phase coupled to wells and the HRPO-labeled anti-dog-32KP annexin-V polyclonal Fab' antibody is not problematic at all in sensitivity for assay of human annexin-V.

The use of the calibration curve as obtained in the subject example (FIG. 12) enabled us to assay annexin-V concentration in the blood, plasma and serum in a highly reproducible and reliable manner from a low concentration to a high concentration, in which there was employed a combination of the monoclonal antibody produced by hybridoma cell line HCA-627 strain deposited as an International Deposit under the number FERM BP-5284 with the HRPO-labeled monocloval antibody produced by hybridoma cell line HDA-907 strain also deposited as an International Deposit under the number FERM BP-5286.

The calibration curve of FIG. 12 was obtained by employing an extremely low concentration of HRPO-labeled anti-annexin-V monoclonal antibody HDA-907-Fab' which may have a HRPO activity of 3 to 4 mU/ml. It is thus possible to provide a more sensitive system.

As can be seen from Table 5 and FIG. 12 on the calibration curve obtained with the standard antigen, the CV values are within 3.6% for four times of measurements of the standard antigen concentration in the range of from a human annexin-V concentration as low as 1 ng/ml up to as high as 100 ng/ml, demonstrating the system enables a highly reproducible assay of annexin-V concentration. From the foregoing, the subject ELISA system using the aforesaid monoclonal antibodies for assay of annexin-V will be fully satisfactory in use as an ELISA system to determine native annexin-V concentration in the human blood.

As shown in FIGS. 1 through 8, in a case where native human annexin-V antigen without 8M-urea-treatment was used as standard antigen in an ELISA system using the combination of the monoclonal antibodies, the absorbance was very small, for example, as in Example 1, only about 5% to about 10% of 8M-urea-treated antigen. By contrast, the ELISA system using the monoclonal antibodies as obtained in the subject example has made a remarkable improvement in reactivity with native human annexin-V antigen.

It was found that the HRPO-labeled Fab' antibodies of the anti-annexin-V monoclonal antibody clones (HDA-676, HDA-907, HDA-1606 and HDA-1937) having a reactivity with human- and dog-annexin-V and selected by the screening operation in the subject example all exhibit a high reactivity with human annexin-V and therefore provide a good combination with HCA-627 as shown in Example 1 in obtaining an excellent calibration curve for human annexin-V antigen concentration.

(8) Possibility of Detection and Quantitative Analysis of Human Annexin-V in Samples by Sandwich ELISA in Which Anti-Human-Annexin-V Monocloval Antibody (HCA-627) and Anti-Native-Human- and Dog-Annexin-V Monocloval Antibody Clone (HDA-907) Are Used From among possible combinations of the monoclonal antibodies as prepared above for use in sensitive assay of native human annexin-V, as a representative was selected the combination of anti-annexin-V monocloval antibody HCA-627 as solid phase coupled to wells and HRPO-labeled anti-annexin-V monocloval antibody HDA-907-Fab to study its application to assay of clinical samples by ELISA.

Thus, into the anti-human-annexin-V monoclonal antibody HCA-627-coupled plates was added, after discarding the blocking solution, reaction buffer solution (sodium phosphate buffer at pH 7.0 containing 1% BSA and 5 mM EDTA)at a rate of 100 microliters per well. An antigen standard solution of native human cardiac mustle-derived annexin-V (0 ng/ml, 1.5625 ng/ml, 3.125 ng/ml, 6.25 ng/ml, 12.5 ng/ml, 25 ng/ml, 50 ng/ml or 100 ng/ml) and a human plasma sample are added each at a rate of 20 microtiters per well, followed by stirring and reaction for one hour at room temperature. Each well was washed four times with the washing solution. Then there was added the HRPO-labeled anti-annexin-V monoclonal antibody HDA-907-Fab' having been prepared to have a concentration of 4 mU/ml as HRPO enzyme activity, at a rate of 100 microliters per well for reaction for thirty minutes at room temperature, followed by washing four times with the washing solution. After the washing the wells were added with OPD substrate solution (containing 0.1M phosphate-citrate buffer added with 2 mg/ml o-phenylenediamine and 4 mM $H_2O_2$) at a rate of 100 microliters per well, followed by absorbance measurements at the primary wanelength 492 nm and at the secondary wanelength 690 nm on an ELISA plate reader.

The human plasma samples were determined for native human annexin-V concentration by reading the calibration curve which was prepared by plotting the absorbance against varying concentration of human cardiac muscle-derived annexin-V as standard antigen. The data for the calibration curve are given in Table 5 and FIG. 12. As mentioned previously, the absorbance increased with increasing concentration of the human annexin-V standard antigen.

(9) Sample Dilution Tests

Dilution tests were performed on a plasma sample prepared by adding purified annexin-V antigen to normal plasma(Sample 1), a plasma sample with a low value of annexin-V concentration (Sample 2) and a plasma sample with a high value of annexin-V concentration (Sample 3). Each sample was subjected to a series of successive doubling dilution. Each series of samples, including the original sample solution, were assayed for annexin-V concentration by the ELISA system for annexin-V assay using the combination of the monoclonal antibody clone HCA-627 as solid phase coupled to well and the HRPO-labeled monoclonal antibody clone HDA-907-Fab'.

The results are given in Table 6, Tables 6-1 through 6-3 and FIG. 13.

TABLE 6

Results of Sample Dilution Tests (Measurements n = 2)

| Sample Dilution | | Human Annexin-V Antigen Measurements (ng/ml) | | |
|---|---|---|---|---|
| Dilution Rate | 1/Dilution Rate | Sample 1 | Sample 2 | Sample 3 |
| × 32 | 0.03125 | 0.97 | | 1.13 |
| × 16 | 0.0625 | 2.37 | 0.20 | 2.71 |
| × 8 | 0.125 | 4.86 | 0.56 | 5.87 |
| × 4 | 0.25 | 9.22 | 1.59 | 11.98 |
| × 2 | 0.5 | 17.85 | 3.52 | 22.63 |
| × 1 | 1 | 35.80 | 6.95 | 42.94 |

TABLE 6-1

Data on Sample 1
(A plasma sample prepared by adding human annexin-V to normal plasma)

| Sample Dilution Rate | Dilution Factor | Number of Measurements | | Average (ng/ml) |
|---|---|---|---|---|
| | | 1 | 2 | |
| × 32 | 0.03125 | 0.95 | 0.99 | 0.97 |
| × 16 | 0.0625 | 2.37 | 2.36 | 2.37 |
| × 8 | 0.125 | 4.89 | 4.82 | 4.86 |
| × 4 | 0.25 | 9.33 | 9.10 | 9.22 |
| × 2 | 0.5 | 18.50 | 17.20 | 17.85 |
| × 1 | 1 | 37.00 | 34.60 | 35.80 |

TABLE 6-2

Data on Sample 2
(A sample having a high value of human annexin-V antigen concentration: KAN-1)

| Sample Dilution Rate | Dilution Factor | Number of Measurements | | Average (ng/ml) |
|---|---|---|---|---|
| | | 1 | 2 | |
| × 32 | 0.03125 | | | |
| × 16 | 0.0625 | 0.19 | 0.21 | 0.20 |
| × 8 | 0.125 | 0.50 | 0.61 | 0.56 |
| × 4 | 0.25 | 1.54 | 1.63 | 1.59 |
| × 2 | 0.5 | 3.51 | 3.53 | 3.52 |
| × 1 | 1 | 6.94 | 6.96 | 6.95 |

TABLE 6-3

Data on Sample 3
(A sample having a high value of human annexin-V antigen concentration: KAN-2)

| Sample Dilution Rate | Dilution Factor | Number of Measurements | | Average (ng/ml) |
|---|---|---|---|---|
| | | 1 | 2 | |
| × 32 | 0.03125 | 1.10 | 1.16 | 1.13 |
| × 16 | 0.0625 | 2.63 | 2.78 | 2.71 |
| × 8 | 0.125 | 5.77 | 5.97 | 5.87 |
| × 4 | 0.25 | 11.94 | 12.01 | 11.98 |

TABLE 6-3-continued

Data on Sample 3
(A sample having a high value of human annexin-V antigen
concentration: KAN-2)

| Sample Dilution Rate | Dilution Factor | Number of Measurements 1 | 2 | Average (ng/ml) |
|---|---|---|---|---|
| ×2 | 0.5 | 22.46 | 22.79 | 22.63 |
| ×1 | 1 | 42.16 | 43.72 | 42.94 |

With Sample 1, a sample prepared by adding annexin-V to normal plasma, the annexin-V concentration in blood varies with the dilution rate, forming a straight dilution line directing toward the origin. With both Sample 2 and Sample 3 (a sample having a high annexin-V concentration), the annexin-V measurement varies in a close relationship with the dilution rate, also forming a substantially straight dilution line directing toward the origin.

Thus, as it was found that the annexin-V measurement is closely related with the dilution rate, forming a straight dilution line directing toward the origin for all samples with or without annexin-V addition, the subject system can provide an assay system for quantitating the annexin-V concentration in samples without interference by possible components in the plasma.

In addition, for the purpose of confirming the reliability of the subject system for assay of clinical samples, recovery tests were conducted by adding human annexin-V as purified annexin-V antigen to plasma and serum samples.

(10) Human Annexin-V Recovery Tests in ELISA System for Assay of Human Annexin-V With respect to the ELISA system as studied above in which there are used anti-annexin-V monoclonal antibody HCA-627 as solid phase coupled to wells and HRPO-labeled anti-annexin-V monoclonal antibody HDA-907-Fab', recovery tests for human annexin-V were conducted to examine whether purified annexin-V antigens as added to plasma or serum are recovered without any influence on the measurements of annexin-V by components present in the plasma or serum.

(11) Procedure for Recovery Test

Purified human annexin-V antigen solutions were prepared to have a concentration of 40.8 ng/ml, 14.6 ng/ml and 4.7 ng/ml. To each of three human plasma samples and two human serum samples was added one of the purified human annexin-V antigens having the three different(high, middle and low) concentrations in a proportion of 9 volumes of sample to 1 volume of antigen to observe annexin-V concentration in each sample. The human annexin-V antigen solution was replaced by buffer solution which was also added to each sample in the same proportion as in the case of human annexin-V antigen, so as to observe human annexin-V concentration in each sample per se. Human annexin-V antigen concentration as added was determined through assay of a sample-like solution prepared by adding human annexin-V antigen to reaction buffer solution instead of the plasma or serum sample in the same proportion as in such sample.

The concentration of human annexin-V recovered was obtained by subtracting measured human annexin-V concentration of a sample per se from measured human annexin-V concentration as added, as given by the following equation(1):

The concentration of annexin-V antigen recovered (ng/ml)=Measured human annexin-V concentration of a sample added with the antigen of the respective concentration (ng/ml)—Measured human annexin-V concentration of the per se (ng/ml)    (1)

The recovery rate at the concentration of annexin-V recovered was obtained by the following equation (2):

Recovery Rate (%)=(Concentration of human annexin-V recovered when added with the antigen of the respective concentration/ Human annexin-V concentration as added)×100    (2)

The results of the recovery tests are summarized in Table 7.

TABLE 7

Results of Recovery Tests

| Type of Sample | Sample Identification No. | Measured Human Annexin-V Concentration in Sample per se (ng/ml) | Measured Human Annexin-V Concentration as Added (ng/ml) | Human Annexin-V Antigen Concentration Recovered (ng/ml) | Measured Human Annexin-V Antigen Concentration in Sample When Added with Human Annexin-V Antigen of the Respective Concentration | | | Human Annexin-V Recovery Rate (%) |
|---|---|---|---|---|---|---|---|---|
| | | | | | Measurement 1 (ng/ml) | Measurement 2 (ng/ml) | Average (ng/ml) | |
| Plasma | KAN-1 | 6.27 | 4.70 | 4.96 | 11.16 | 11.30 | 11.23 | 105.5 |
| | | | 14.60 | 14.08 | 20.10 | 20.59 | 20.35 | 96.4 |
| | | | 40.81 | 39.64 | 46.18 | 45.63 | 45.91 | 97.1 |
| Plasma | KAN-2 | 42.00 | 4.70 | 5.11 | 45.30 | 48.91 | 47.11 | 108.6 |
| | | | 14.60 | 15.37 | 55.82 | 58.91 | 57.37 | 105.2 |
| | | | 40.81 | 44.84 | 85.28 | 88.40 | 86.84 | 109.9 |
| Plasma | TK | 1.27 | 4.70 | 5.01 | 6.14 | 6.41 | 6.28 | 106.5 |
| | | | 14.60 | 14.98 | 15.98 | 16.52 | 16.25 | 102.6 |
| | | | 40.81 | 39.07 | 39.34 | 41.34 | 40.34 | 95.7 |
| Serum | 93011 | 1.59 | 4.70 | 4.75 | 6.39 | 6.28 | 6.34 | 101.0 |
| | | | 14.60 | 13.38 | 14.97 | 14.96 | 14.97 | 91.6 |
| | | | 40.81 | 36.93 | 38.96 | 38.08 | 38.52 | 90.5 |
| Serum | 93025 | 1.57 | 4.70 | 4.96 | 6.55 | 6.51 | 6.53 | 105.5 |
| | | | 14.60 | 14.42 | 15.98 | 16.00 | 15.99 | 98.8 |
| | | | 40.81 | 39.94 | 40.92 | 42.09 | 41.51 | 97.9 |

The result of the recovery test was excellent in the plasma samples with from a low value (1.27 ng/ml) up to a high value (42.0 mg/ml) of annexin-V concentration in sample per se. as the antigen recovery rate was between 96% and 109% in the concentration range of human annexin-V antigen added (from 4.7 ng/ml to 40.8 ng/ml).

The recovery rate was also excellent with respect to the serum samples, as it was between 91% and 106% in the concentration range of human annexin-V antigen added, i.e. from a low concentration (4.7 ng/ml) up to a high concentration (40.8 ng/ml).

As can be seen from the foregoing, the subject ELISA system for assay of annexin-V has a good prospect of application to the assay of clinical samples because it has enabled reliable quantitative analysis without being influenced by components of the plasma and serum.

EXAMPLE 11

Application of the Present Invention to Analysis of Blood Sample by Enzyme Antibody Method (1) Pretreatment of Collected Blood Intvavenuously collected whole blood was placed without delay into a 1.8 ml collecting tube containing 0.2 ml of 3.8% sodium citrate, followed by mild stirring and centrifugation at 2500 rpm for 10 minute to isolate plasma. The isolated plasma was immediately or, following after frozen for keeping until use for keeping, supplied for use in the assay of annexin-V concentration.

In the case when EDTA salt is used in place of sodium citrate, 3 to 5 mM EDTA 2 potassium or EDTA 2 sodium may be placed in the blood collecting tube to isolate plasma following centrifugation.

(2) Diagnosis of Myocardial Infarction

Analysis of blood collected three hours after the onset from a 72-year-old lady and having no symptom of hemolysis indicated CK (creatine phosphate enzyme) value of 50 U/L, a normal value, and annexin-V concentration in plasma of 16.4 ng/ml, an increased value. The case was later affirmatively diagnostic of myocardial infection because of elevation of CK value up to 1108 U/L and a typical abnormality on the electrocardiogram. Annexin-V concentration in plasma returned to a normal value three days after the onset of the disease.

This case indicates that the assay of annexin-V concentration in plasma in the first sampling of blood with no hemolysis is of use in diagnosis of myocardial infarction. Annexin-V concentration in plasma of a patient with myocardial infection is relatively high in an early stage of the disease (within 6 hours after the onset of attack). From the analysis of blood samples without homolysis from patients complaining of pains in the chest, it was later established that 70% of the cases, where annexin-V concentration in blood was determined to show 10 ng/ml or more, is diagnostic of myocardial infarction.

(3) Diagnosis of Angina Pectoris

Blood with no hemolysis from a 55-year-old man who complained of a pain in the chest three hours after a first pain, was collected three and a half hours after the onset and analyzed for annexin-V concentration in plasma, with the result that the concentration was 5.8 ng/ml. Analysis was also conducted on blood samples from the same patient thereafter for CK values in the blood with the result that the values were 140 U/L or less, all a normal value. Coronary angiography taken later showed a high degree of stenosis on the right coronary artery. Thus, based on this fact with reference to the clinical symtoms, the case was affirmatively diagnosed as angina pectoris.

This case demonstrates that the analysis of blood with no hemolysis to determine annexin-V concentration in plasma is of use in the diagnosis of angina pectoris. While annexin-V concentration in plasma of a patient with annexin-V angina pectoris is relatively low as compared with a case of myocardial infarction, approx. 70% of cases, where CK value of a patient complaining of pains in the chest was not diagnostic of angina pectoris but the annexin-V concentration in plasma showed 5 ng/ml or more, were diagnosed as angina pectoris.

(4) Annexin-V Concentration in Normal Adults

Annexin-V concentration in plasma from blood with no hemolysis of normal males 22 to 75 years of age is in the range of 0.6 to 1.9 ng/ml, whereas that of normal females 24 to 78 years of age is in the range of 0.5 to 1.7 ng/ml, with the average being 1.0 ng/ml, the maximum 1.9 ng/ml and the minimum 0.5 ng/ml. There was observed neither sex-dependent nor age-dependent variations.

Hemolysis will bring a higher value of annexin-V concentration measurement in plasma because annexin-V leaks into the plasma from the decomposed leukocytes, platelets and erythrocytes. In treating blood sample following the collection, care should therefore be taken not to cause hemolysis to occur, for example, through use of a fine collecting needle or avoidance of vigorous shaking of blood samples. Slight hemolysis will give no substantial influence on the assay of annexin-V concentration in blood, enabling such assay. Thus, the assay of annexin-V concentration in plasma is of use in the diagnosis of myocardial and angina pectoris.

(5) Comparison with Example 7

In Example 7 the numerical values of analysis, including the normal values, are somewhat higher than those in Example 9. This is because the analysis in Example 7 includes measurement of annexin-V concentration due to hemolysis which have occurred during the treatment of the blood samples.

Example 7 therefore suggests that, as long as blood samples are treated in the same manner, assay of annexin-V concentration in plasma is of use in the diagnosis of myocardial infarction and angina pectoris even if hemolysis occurs.

(6) As can be seen from the description of the invention, anti-human-annexin-V monoclonal antibody HCA-627 and anti-human-annexin-V monoclonal antibody HDA-907 obtained by the present invention are monoclonal antibodies which are capable of specifically recognizing an annexin-V antigenic molecule through different antigenic determinants on an identical annexin-V molecule.

The sandwich ELISA system using the two monoclonal antibodies enables the assay of annexin-V antigen in a highly sensitive manner, providing excellent quantitative analysis as can be seen from the satisfactory results of the dilution tests and the recovery tests.

In addition, the two monoclonal antibodies are capable of cross-reacting with both human-annexin-V antigen and dog annexin-V antigen. The two cross-reacting monoclonal antibodies are considered to recognize antigenic determinants common to the different types of annexin-V antigen molecules. Thus, in preparing standard antigen for assay annexin-V, such monoclonal antibodies make it possible to provide less expensive dog-derived annexin-V without causing the ethical issue with respect to extraction and purification of human-derived annexin-V.

Industrial Applicability

The present invention is directed to the production of novel anti-human-annexin-V monoclonal antibodies by culturing hybridoma cell lines HCA-627 strain (deposited on Nov. 6, 1995 as an International Deposit under the number FERM BP-5284 at the National Institute of Bioscience and Human-Technology, the Agency of Industrial Science and Technology of Japan, at Higashi 1-1-3, Tukuba-City, Ibaraki-Pref., Japan, an International Depositary Authority for the deposit of microorganisms) and HDA-907 strain (deposited on Nov. 7, 1995 as an International Deposit under the number FERM BP-5286 at the National Institute of Bioscience and Human-Technology, the Agency of Industrial Science and Technology of Japan, at Higashi 1-1-3, Tukuba-City, Ibaraki-Pref., Japan, an International Depositary Authority for the deposit of microorganisms), in which the hybridoma cells were prepared by extracting lymphocytic plasmablast cells from lymphoid organs of mammalian animals such as mice immunized with human annexin-V, an antigenic protein from human heart, and fusing lymphocytic plasmablast cells with myeloma cells.

The anti-human-annexin-V monoclonal antibodies obtained in the present invention are ones capable of recognizing specifically human annexin-V as the antigenic protein.

In addition to the anti-human-annexin-V monoclonal antibodies there can be also obtained, according to the present invention, anti-annexin-V monoclonal antibodies which will cross-react with annexin-V as antigenic protein derived from various animals (e.g. beagles and rats).

These cross-reacting anti-annexin-V monoclonal antibodies are considered to have an ability to recognize antigenic determinant sites occurring commonly on the annexin-V protein molecules. Such sites having antigenic determinants common to the annexin-V protein molecules are important ones for maintaining the molecular structure of annexin-V reserved among different animal species.

The use of the anti-human-annexin-V monoclonal antibodies of the present invention makes it possible to diagnose patients with ischemic diseases such as myocardial infarction and angina pectoris by means of ELISA, for example, through the measurement of human annexin-V concentration in the blood. Thus, although conventionally thought impossible, myocardial infarction and angina pectoris can be diagnosed quickly and reliably even at the early stages of the diseases, and the reliable diagnosis can be conducted free of influence by rheumatoid factor.

Another exemplarly advantage of the present invention is that it can be applied in autopsy or post mortem to stain the cardiac muscle tissue using the anti-human-annexin-V monoclonal antibodies so as to detect the distribution of human annexin-V through the cardiac muscle tissue.

In a further aspect of the present invention, there can be obtained anti-human-annexin-V monoclonal antibodies which are different in reactivity and are capable of recognizing different antigenic determinants on a human annexin-V molecule. By selecting, from a group of such anti-human-annexin-V monoclonal antibodies, two different types of anti-human-annexin-V monoclonal antibodies different from each other in antigenic determinant for recognition and combining them, it is possible to determine human annexin-V with a high sensitivity and reproducibility by means of ELISA.

Thus, by the combination of the anti-human-annexin-V monoclonal antibodies having different specificities to different antigenic determinants, preparation is now possible of highly reliable reagents for the assay of myocardial infarction and angina pectoris.

The anti-human-annexin-V monoclonal antibodies of the present invention are also suitable for use in tissue-staining, in addition to their use in the ELISA system for the assay of human annexin-V. Through the tissue-staining analysis, it is possible to identify the areas in the myocardial tissue of human heart where human anexin localizes or distributes, and of the areas where human annexin-V passes from the myocardial tissue due to ischemia, thereby greatly contributing to molecular physiological and other studies. It is also possible to recover annexin-V molecules of a high purity from the tissue extracts through the purification by means of affinity chromatography using the anti-human-annexin-V monoclonal antibodies or the anti-annexin-V monoclonal antibodies. Further, identification of annexin-V molecules can be made by means of Western blotting.

As can be seen from the above, the anti-human-annexin-V monoclonal antibodies and the anti-annexin-V monoclonal antibodies obtained from various animals according to the present invention can be used in molecular and physiological studies on annexin-V occurring in humans and various animals, thereby making a great contribution in the wide range of areas including both basic medicine and clinical medicine.

We claim:

1. An anti-annexin-V monoclonal antibody produced by a hybridoma cell line which is selected from the group consisting of the hybridoma cell lines deposited as FERM BP-5284 and FERM BP-5286 at the International Depository Authority for the deposit of microorganisms, said anti-annexin-V monoclonal antibody being cross-reactive with annexin-V from the heart cells of one or more mammalian species.

2. A hydridoma cell line selected from the group consisting of the hybridoma cell lines deposited as FERM BP-5284 and FERM BP-5286 at the International depository Authority for the deposit of microorganisms, said hybridoma cell line having the ability to produce an anti-annexin-V monoclonal antibody which has a binding specificity to an antigenic determinant on annexin-V antigenic protein and which is capable of cross-reacting with annexin-V from the heart of one or more mammalian species.

3. A diagnostic agent for myocardial infarction and angina pectoris which comprises:

a first reagent containing a first anti-annexin-V monoclonal antibody being produced by a hybridoma cell line selected from the group consisting of the hybridoma cell lines deposited as FERM BP-5284 and FERM BP-5286 at the International Depository Authority for the deposit of microorganisms;

a second reagent containing a second anti-annexin-V monoclonal antibody being produced by the other hybridoma cell line selected from said group, or polyclonal antibody, wherein the antibody of the second reagent is labeled;

wherein the antibodies of both reagents are cross-reactive with annexin-V from human heart cells and the annexin-V antigen is annexin-V from heart cells of one or more mammalian species.

4. The diagnostic agent for myocardial infarction and angina pectoris of claim 3 in which the first anti-annexin-V monoclonal antibody is anti-annexin-V monoclonal antibody produced by the hybridoma cell line FERM BP-5284 and the labeled second anti-annexin-V monoclonal antibody is produced by labeling the anti-annexin-V monoclonal antibody produced by the hybridoma cell line FERM BP-5286.

5. The diagnostic agent for myocardial infarction and angina pectoris of claim 3 in which the first anti-annexin-V monoclonal antibody is anti-annexin-V monoclonal antibody produced by the hybridoma cell line FERM B-5286 and the labeled second anti-annexin-V monoclonal antibody is produced by labeling the anti-annexin-V monoclonal antibody produced by the hybridoma cell line FERM BP-5284.

6. The diagnostic agent for myocardial infarction and angina pectoris of claim 3 in which the first anti-annexin-V monoclonal antibody is anti-annexin-V monoclonal antibody produced by the hybridoma cell line FERM BP-5284 and the labeled second anti-annexin-V polyclonal antibody is anti-dog-annexin-V antibody which cross-reacts with human annexin-V.

7. The diagnostic agent for myocardial infarction and angina pectoris of claim 3 in which the first anti-annexin-V monoclonal antibody is anti-annexin-V monoclonal antibody produced by the hybridoma cell line FERM BP-5286 and the labeled second anti-annexin-V polyclonal antibody is anti-dog-annexin-V antibody which cross-reacts with human annexin-V.

8. A method for diagnosing myocardial infarction and angina pectoris comprising the steps of:

causing an antigen-antibody reaction of annexin-V in a sample with a first anti-annexin-V monoclonal antibody to form an annexin-V antigen/anti-annexin-V monoclonal antibody complex;

allowing the antigenic site of annexin-V of the formed annexin-V antigen/anti-annexin-V monoclonal antibody complex to be bound with a labeled second anti-annexin-V monoclonal antibody or labeled anti-annexin-V polyclonal antibody so as to form a labeled form of said annexin-V antigen/anti-annexin-V monoclonal antibody complex bound with the polyclonal or monoclonal antibody; and quantitatively analyzing the labeled form of said complex to perform said diagnosis.

9. The method of diagnosing myocardial infarction or angina pectoris of claim 8 in which the first anti-annexin-V monoclonal antibody is produced by a hybridoma cell line selected from the group consisting of the hybridoma cell lines deposited as FERM BP-5284 and FERM BP-5286 at the International Depository Authority for the deposit of microorganisms, and the labeled second anti-annexin-V monoclonal antibody is produced by labeling the second anti-annexin-V monoclonal antibody produced being different from the first anti-annexin-V monoclonal antibody produced by a hybridoma cell line which is selected from the same said group, wherein said first and second anti-annexin monoclonal antibodies have a binding specificity for an antigenic determinant on annexin-V protein from human heart cells.

10. The method for diagnosing myocardial infarction and angina pectoris of claim 8 in which the first anti-annexin-V monoclonal antibody is anti-annexin-V monoclonal antibody produced by the hydridoma cell line FERM BP-5284.

11. The method for diagnosing myocardial infarction and angina pectoris of claim 8 in which the first anti-annexin-V monoclonal antibody is anti-annexin-V monoclonal antibody produced by the hybridoma cell line FERM BP-5286.

12. The method for diagnosing myocardial infarction and angina pectoris of claim 8 in which the labeled second anti-annexin-V monoclonal antibody is anti-annexin-V monoclonal antibody produced by the hybridoma cell line FERM BP-5284.

13. The method for diagnosing myocardial infarction angina pectoris of claim 8 in which the labeled second anti-annexin-V monoclonal antibody is anti-annexin-V monoclonal antibody produced by the hybridoma cell line FERM BP-5286.

14. A method for analyzing annexin-V in human cardiac muscle or in a sample which comprises causing an antigen-antibody reaction of human annexin-V in the human cardiac muscle or the sample with an anti-annexin-V monoclonal antibody produced by a hybridoma cell line selected from the group consisting of the hybridoma cell lines deposited as FERM BP-5284 and FERM BP-5286 at the International Depository Authority for the deposit of microorganisms, to form an annexin-V antigen-anti-annexin-V monoclonal antibody complex and quantitatively analyzing the formed annexin V antigen-anti-annexin-V monoclonal antibody complex.

15. A method for analyzing annexin-V in a sample which comprises the steps of:

causing an antigen-antibody reaction of human annexin-V in the sample with a first anti-annexin-V monoclonal antibody produced by a hybridoma cell line selected from the group consisting of the hybridoma cell lines deposited as FERM BP-5284 and FERM BP-5286 at the International Depository Authority for the deposit of microorganisms to form an annexin-V antigen-anti-annexin-V monoclonal antibody complex, allowing the antigenic site of human annexin-V of the formed annexin-V antigenic-anti-annexin-V monoclonal antibody complex to be bound with a labeled second anti-annexin-V monoclonal antibody or anti-annexin-V polyclonal antibody, so as to form a labeled from of said annexin-V antigen-anti-annexin-V monoclonal polyclonal antibody complex bound with labeled anti-annexin-V polyclonal antibody or labeled the second anti-annexin-V monoclonal antibody;

quantitatively analyzing the labeled form of the complex and;

said labeled second anti-annexin monoclonal antibody is produced by labeling second anti-annexin-V monoclonal antibody being different from the first anti-annexin-V monoclonal antibody and produced by a hybridoma cell line which is selected from the group consisting of the hybridoma cell line deposited as FERM BP-5284 and FERM BP-5286 at the International Depository Authority for the deposit of microorganisms.

16. The method of claim 15 in which the first anti-annexin-V monoclonal antibody is one produced by the hybridoma cell line FERM BP-5284 and has a binding specificity for an antigenic determinant on human annexin-V antigenic protein.

17. The method of claim 15 in which the first anti-annexin-V monoclonal antibody is one produced by the hybridoma cell line FERM BP-5286 and has a binding specificity for an antigenic determinant on human annexin-V antigenic protein.

18. The method of claim 15 in which the labeled second anti-annexin-V monoclonal antibody is produced by labeling the anti-annexin-V monoclonal antibody produced by hybridoma cell line FERM BP-5284 and has a binding specificity for an antigenic determinant on human annexin-V antigenic protein.

19. The method of claim 15 in which the labeled second anti-annexin-V monoclonal antibody is produced by labeling the anti-annexin-V monoclonal antibody produced by hybridoma cell line FERM BP-5286 at and has a binding specificity for an antigenic determinant on human annexin-V antigenic protein.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Glu Tyr Gly Ser Ser Leu Glu
1               5

( 2 ) INFORMATION FOR SEQ ID NO:2:

( i ) SEQUENCE CHARACTERISTICS:
( A ) LENGTH: 13 amino acids
( B ) TYPE: amino acid
( C ) STRANDEDNESS:
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Gly Thr Asp Glu Glu Lys Phe Ile Thr Ile Phe Gly Thr
1               5                   10